(12) United States Patent
Chen

(10) Patent No.: US 9,153,404 B2
(45) Date of Patent: Oct. 6, 2015

(54) CHARGED PARTICLE BEAM SCANNING USING DEFORMED HIGH GRADIENT INSULATOR

(71) Applicant: Lawrence Livermore National Security, LLC, Livermore, CA (US)

(72) Inventor: Yu-Jiuan Chen, Fremont, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 13/705,084

(22) Filed: Dec. 4, 2012

(65) Prior Publication Data

US 2013/0140468 A1 Jun. 6, 2013

Related U.S. Application Data

(60) Provisional application No. 61/566,986, filed on Dec. 5, 2011.

(51) Int. Cl.
*H01J 3/26* (2006.01)
*A61N 5/10* (2006.01)
*G21K 1/087* (2006.01)

(52) U.S. Cl.
CPC ............... *H01J 3/26* (2013.01); *A61N 5/1043* (2013.01); *A61N 5/1077* (2013.01); *G21K 1/087* (2013.01); *A61N 2005/1087* (2013.01)

(58) Field of Classification Search
CPC ............... H01J 3/26; H01J 3/03; H01J 29/80; H01J 29/803; H01J 29/826; H01J 49/061
USPC ................... 250/396 R, 492.1, 492.2, 492.3; 315/505
See application file for complete search history.

(56) References Cited

U.S. PATENT DOCUMENTS

| | | | | |
|---|---|---|---|---|
| 3,308,323 | A | * | 3/1967 | De Graaff .................. 313/360.1 |
| 5,120,956 | A | * | 6/1992 | Purser .......................... 250/281 |
| 5,434,609 | A | | 7/1995 | Rhodes |
| 5,811,944 | A | * | 9/1998 | Sampayan et al. ............ 315/505 |
| 5,821,705 | A | * | 10/1998 | Caporaso et al. ............. 315/507 |
| 6,331,194 | B1 | * | 12/2001 | Sampayan et al. ........... 29/25.03 |
| 7,330,533 | B2 | * | 2/2008 | Sampayon .................... 378/119 |
| 7,576,499 | B2 | * | 8/2009 | Caporaso et al. ............. 315/505 |

(Continued)

OTHER PUBLICATIONS

International Search Report and Written Opinion mailed on Mar. 25, 2013 for International Application No. PCT/US2012/067807, filed Dec. 4, 2012 (7 pages).

*Primary Examiner* — Michael Logie
*Assistant Examiner* — Jason McCormack
(74) *Attorney, Agent, or Firm* — Perkins Coie LLP

(57) ABSTRACT

Devices and methods are provided to allow rapid deflection of a charged particle beam. The disclosed devices can, for example, be used as part of a hadron therapy system to allow scanning of a target area within a patient's body. The disclosed charged particle beam deflectors include a dielectric wall accelerator (DWA) with a hollow center and a dielectric wall that is substantially parallel to a z-axis that runs through the hollow center. The dielectric wall includes one or more deformed high gradient insulators (HGIs) that are configured to produce an electric field with an component in a direction perpendicular to the z-axis. A control component is also provided to establish the electric field component in the direction perpendicular to the z-axis and to control deflection of a charged particle beam in the direction perpendicular to the z-axis as the charged particle beam travels through the hollow center of the DWA.

25 Claims, 18 Drawing Sheets

(56) References Cited

U.S. PATENT DOCUMENTS

| | | |
|---|---|---|
| 7,710,051 B2* | 5/2010 | Caporaso et al. ............ 315/505 |
| 2004/0056207 A1 | 3/2004 | Petrov et al. |
| 2006/0022152 A1* | 2/2006 | Natori et al. ............... 250/493.1 |
| 2007/0045534 A1 | 3/2007 | Zani et al. |
| 2009/0224700 A1* | 9/2009 | Chen et al. ................... 315/505 |
| 2009/0314949 A1 | 12/2009 | Plettner et al. |
| 2010/0074408 A1* | 3/2010 | Bert et al. ...................... 378/65 |
| 2011/0073759 A1 | 3/2011 | Harada et al. |
| 2011/0297841 A1* | 12/2011 | Caporaso et al. ...... 250/396 ML |

* cited by examiner

CHARGED PARTICLE BEAM SCANNING USING DEFORMED HIGH GRADIENT INSULATOR

CROSS REFERENCE TO RELATED APPLICATIONS

This patent application claims the benefit of U.S. Provisional Patent Application No. 61/566,986, filed on Dec. 5, 2011. The entire content of the before-mentioned patent application is incorporated by reference

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

The present application generally relates to charged particle beams and, more particularly, to methods and devices for controlling the deflection of charged particle beams.

BACKGROUND

Particle accelerators are used to increase the energy of electrically-charged particles, e.g., electrons, protons, or charged atomic nuclei. High energy electrically-charged particles can be used in various application. For example, high energy electrically-charged particles can accelerated to collide with a target such as atoms or molecules to break up the nuclei of the target atoms or molecules and interact with other particles. The resulting products are observed with a detector. At very high energies the accelerated charged particles can cause transformations in a target caused by the collision which can be used to discern the nature and behavior of fundamental units of matter. Particle accelerators are also important tools in the effort to develop nuclear fusion devices, and in medical applications such as proton therapy for cancer treatment, which is also known as hadron therapy.

In various applications, the beam of the charged particles output by an accelerator may be scanned to change its direction. For example, such beam scanning is desirable in directing protons to desired regions in a target tissue in proton cancer treatment such as the Intensity Modulated Hadron Therapy. Some hadron therapy centers place a mask in front of the patient to manipulate the distribution of the dose deposited in the tumor. However, neutron generation in the mask is a concern for secondary cancers. In some hadron therapy techniques that are free of masks, beam scanning is carried out through a combination of mechanical movement of the machine and/or the patient's bed and a large bending magnet at the end of the hadron machine. These types of scanning systems are large in size and heavy in weight. Additionally, it may be difficult to quickly change scan settings for the robotic couch/bed, the machine or the bending magnets, thus rendering beam scanning unpractical during a single treatment session.

SUMMARY

The disclosed embodiments relate to providing methods and devices that allow rapid and dynamic deflection of a charged particle beam. One aspect of the disclosed embodiments relates to a charged particle beam deflector, comprising a dielectric wall accelerator (DWA) having a hollow center and including a dielectric wall that is substantially parallel to a z-axis that runs through the hollow center, the dielectric wall comprising one or more deformed high gradient insulators (HGIs) configured to produce an electric field comprising a component in a direction perpendicular to the z-axis. The charged particle beam deflector also includes a control component configured to establish the component of the electric field in the direction perpendicular to the z-axis and to control deflection of a charged particle beam in the direction perpendicular to the z-axis as the charged particle beam travels through the hollow center.

In one exemplary embodiment, the one or more HGIs comprise a deformed grooved HGI, the deformed grooved HGI comprising periodic grooves that are structured as part of a dielectric material and are arranged to form a slant angle, $\theta$, with respect to an axis normal to the z-axis. In another exemplary embodiment, the one or more HGIs comprise a deformed multilayer HGI comprising alternating dielectric and conductor materials that are arranged to form a slant angle, $\theta$, with respect to an axis normal to the z-axis. In one exemplary embodiment, the one or more HGIs comprise a deformable multilayer HGI comprising alternating dielectric and conductor materials that are arranged to form a changeable slant angle, $\theta$, with respect to an axis normal to the z-axis.

According to one exemplary embodiment, the DWA comprises a first deformed HGI and a second HGI arranged in a cascade fashion. In this exemplary embodiment, the control component is configured to establish: at least a portion of the component of the electric field in the direction perpendicular to the z-axis across the first deformed HGI, a first axial component of the electric field along the z-axis across the first deformed HGI, and a second axial component of the electric field along the z-axis across the second HGI that is opposite in direction to the first axial component. In another exemplary embodiment, the control component is configured to establish the first and the second axial components such that the charged particle beam experiences substantially zero net acceleration after traveling through the hollow center of both HGIs. In yet another exemplary embodiment, the second HGI is one of a normal HGI and a deformed HGI.

In one exemplary embodiment, the DWA comprises a first deformed grooved HGI. In this exemplary embodiment, the control component is configured to establish: at least a portion of the component of the electric field in the direction perpendicular to the z-axis across the deformed grooved HGI, and a first axial component of the electric field along the z-axis across the first deformed grooved HGI. In another exemplary embodiment, the control component is configured to apply one or more voltages to the DWA for establishing the electric field. For example, the control component is configured vary the applied voltage(s) to modify the electric field strength.

In another exemplary embodiment, the control component comprises one or more moveable mechanical components that are configured to rearrange physical characteristics of a deformable HGI, and to thereby change at least a slant angle, $\theta$, of alternating dielectric and conductor materials of the deformable HGI with respect to an axis normal to the z-axis. According to another embodiment, at least one of the one or more deformed HGIs is configured to be rotated around the z-axis.

Another exemplary embodiment relates to a radiation therapy system that comprises the above noted charged particle beam deflector. In this exemplary embodiment, the one or more deformed HGIs constitute a section of the DWA that includes additional sections comprising normal HGIs. In another example embodiment, the one or more deformed HGIs constitute a mechanism for diverting the charged particle beam from one therapy room to another therapy room and/or around a patient's location. In still another exemplary embodiment, the charged particle beam deflector is configured to allow scanning of the charged particle beam across a target area.

Another aspect of the disclosed embodiments relates to a method for scanning a charged particle beam that includes applying one or more voltages to a dielectric wall accelerator (DWA) having a hollow center and including a dielectric wall that is substantially parallel to a z-axis that runs through the hollow center. The dielectric wall comprises one or more deformed high gradient insulators (HGIs) configured to produce an electric field comprising a component in a direction perpendicular to the z-axis, where the applied one or more voltages establishes the electric field. This method further comprises varying the applied one or more voltages to control deflection of a charged particle beam in the direction perpendicular to the z-axis as the charged particle beam travels through the hollow center.

In one exemplary embodiment, the DWA comprises a deformed grooved HGI, the deformed grooved HGI comprising periodic grooves that are structured as part of a dielectric material and are arranged to form a slant angle, θ, with respect to an axis normal to the z-axis. In this exemplary embodiment, varying the applied one or more voltages varies the strength of the electric field component in the direction perpendicular to the z-axis.

In another exemplary embodiment, the DWA comprises a deformed multilayer HGI comprising alternating dielectric and conductor materials that are arranged to form a slant angle, θ, with respect to an axis normal to the z-axis. In this exemplary embodiment, varying the applied one or more voltages varies the strength of the electric field component in the direction perpendicular to the z-axis.

In yet another exemplary embodiment, the DWA comprises a deformable multilayer HGI comprising alternating dielectric and conductor materials that are arranged to form a changeable slant angle, θ, with respect to an axis normal to the z-axis. In this exemplary embodiment, varying the applied one or more voltages varies the strength of the electric field component in the direction perpendicular to the z-axis, and the method further comprises changing at least the slant angle using moveable mechanical components that are configured to rearrange physical characteristics of the deformable HGI.

According to another exemplary embodiment, the DWA comprises a first deformed HGI and a second HGI arranged in a cascade fashion. In this exemplary embodiment, applying the one or more voltages comprises: applying a first voltage to establish at least a portion of the component of the electric field in the direction perpendicular to the z-axis across the first deformed HGI and a first axial component of the electric field along the z-axis across the first deformed HGI, and applying a second voltage to establish a second axial component of the electric field along the z-axis across the second HGI that is opposite in direction to the first axial component. In one exemplary embodiment, the first and the second voltage values are selected to establish the first and the second axial components such that the charged particle beam experiences substantially zero net acceleration after traveling through the hollow center of both HGIs.

In another exemplary embodiment, the DWA comprises a first deformed grooved HGI. In this exemplary embodiment, applying the one or more voltages comprises applying a first voltage to establish at least a portion of the component of the electric field in the direction perpendicular to the z-axis across the first deformed grooved HGI and a first axial component of the electric field along the z-axis across the first deformed grooved HGI.

According to still another exemplary embodiment, varying the one or more voltages comprises: applying a first voltage to establish a first electric field component in the direction perpendicular to the z-axis and to thereby cause the charged particle beam to be deflected to a first position in an x-y plane that is perpendicular to the z-axis, as well as applying a second voltage to establish a second electric field component in the direction perpendicular to the z-axis and to thereby cause the charged particle beam to be deflected to a second position in the x-y plane. In one exemplary embodiment, the DWA comprises a deformable HGI and the above noted method further comprises causing physical movement of alternating dielectric and conductor materials of the deformable HGI to change at least a slant angle, θ, of the of alternating dielectric and conductor materials with respect to an axis normal to the z-axis, and to thereby further controlling the deflection of the charged particle beam. In yet another exemplary embodiment, the above noted method further comprises rotating at least one of the one or more HGIs to cause the charged particle beam's deflection from a first location to a second location in an x-y plane that is perpendicular to the z-axis

DETAILED DESCRIPTION

Figure 1:
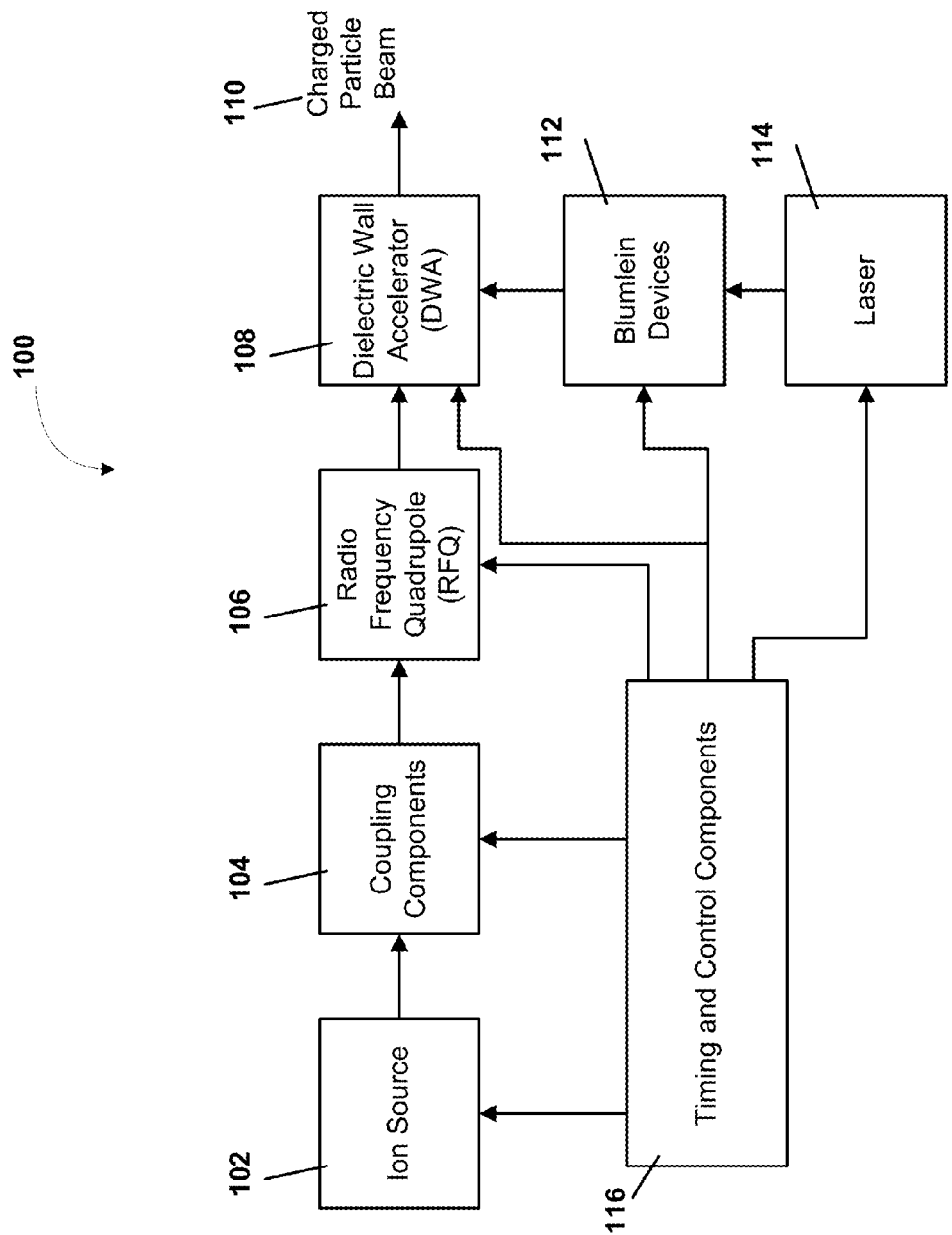
FIG. 1 illustrates a simplified diagram of an exemplary linear particle accelerator that can accommodate the disclosed embodiments.

FIG. 1 illustrates a simplified diagram of an exemplary linear particle accelerator (linac) 100 that can be used to accommodate the disclosed embodiments. For simplicity, FIG. 1 only depicts some of the components of the linac 100. Therefore, it is understood that the linac 100 can include additional components that are not specifically shown in FIG. 1. An ion source 102 produces a proton beam that is coupled to a radio frequency quadrupole (RFQ) 106 using coupling components 104. The RFQ 106 provides focusing, bunching and acceleration for the proton beam. One exemplary configuration of a radio frequency quadrupole includes an arrangement of four triangular-shaped vanes that form a small hole, through which the proton beam passes. The edges of the vanes at the central hole include ripples that provide acceleration and shaping of the beam. The vanes are RF excited to accelerate and shape the ion beam passing therethrough. The beam output by RFQ 106 is coupled to a dielectric wall accelerator (DWA) 108 that provides accelerating electric field along the longitudinal direction of the DWA 108 which further accelerates protons in the proton beam to produce the output charged particle beam 110. FIG. 1 also shows Blumlein devices 112 and the associated laser 114 that are used to deliver voltage pulses to the DWA 108 by switches, e.g., using laser light to trigger photonic switches for controlling the DWA 108. The timing and control components 116 provide the necessary timing and control signals to various components of the linac 100 to ensure proper operation and synchronization of those components.

The timing and control components 116 can be implemented in-part, or be controlled, by hardware and/or software components that can include a processor and a memory that is in communication with the processor. For example, the memory can include processor executable code embodied thereupon, which when executed by the processor, provides the timing and control components 116, as well as other electronic and electro-mechanical components, with various commands, data or other information. The timing and control components 116 may also include one or more moveable mechanical components, and the associated electronic and/or mechanical components, that facilitate control and/or operations of the linac 100. For example, as will be described in the sections that follow, such mechanical components may allow rearrangement of physical characteristics of particular sections of the DWA 108.

Figure 2A:
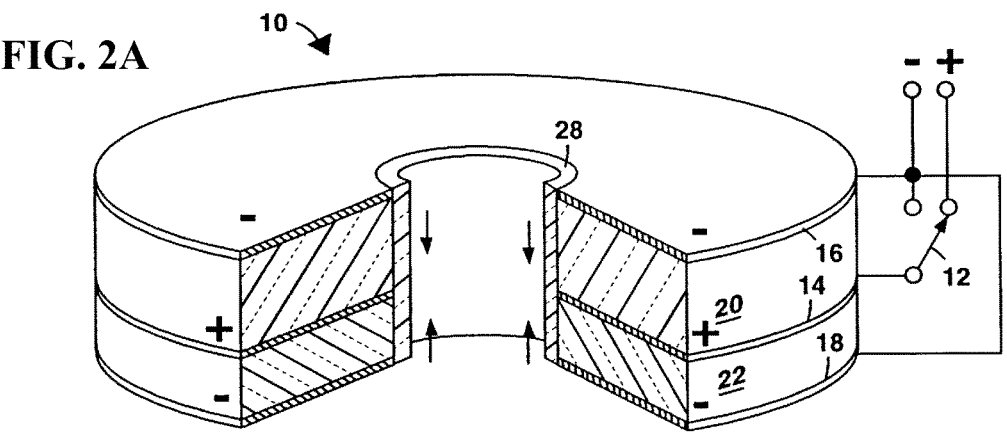
FIG. 2A illustrate an operation of a single dielectric wall accelerator cell that can be utilized with the accelerator of FIG. 1.
Figure 2B:
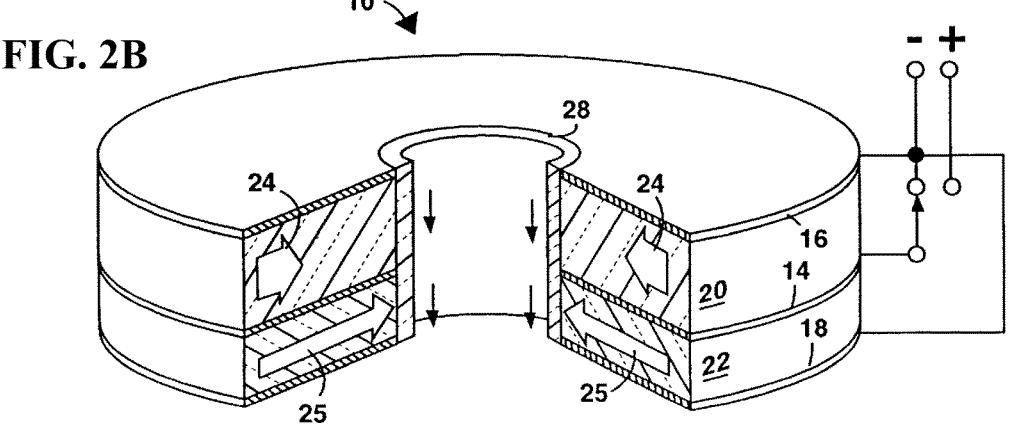
FIG. 2B illustrate another phase of operation of the single dielectric wall accelerator cell of FIG. 2A.
Figure 2C:
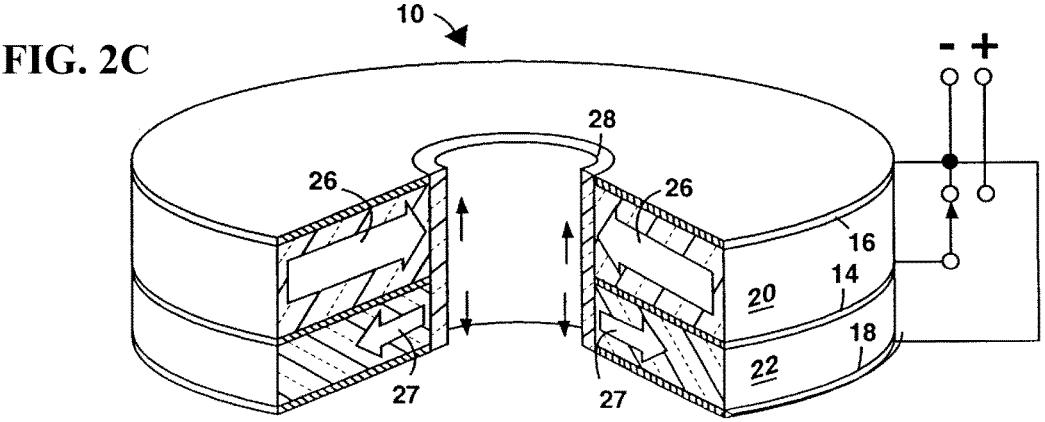
FIG. 2C illustrate another phase of operation of the single dielectric wall accelerator cell of FIG. 2B.
Figure 2D:
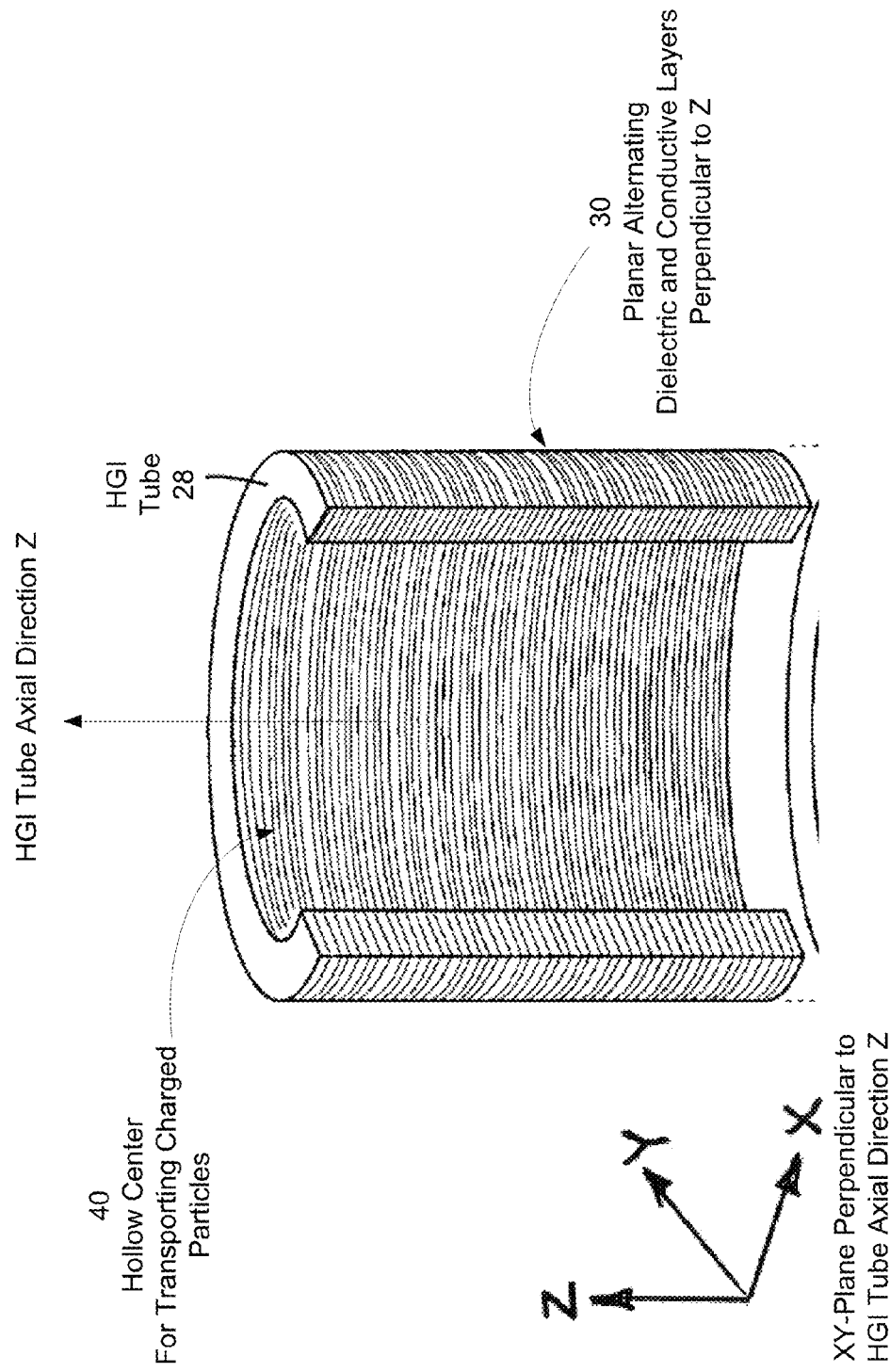
FIG. 2D illustrate a dielectric wall accelerator cell that includes alternating layers of dielectric and conductive layers.

FIG. 2A, FIG. 2B and FIG. 2C provide exemplary diagrams that illustrate the operation of a single DWA cell 10 under the control of a switch 12, powered by a radial transmission line, that can be utilized as the building block for the DWA 108 with the linac 100 of FIG. 1. FIG. 2D shows an example of the dielectric sleeve 28 of the DWA in a high gradient insulator (HGI) structure, which is a layered insulator 30 having alternating electrically conductive materials (e.g., metal conductors) and dielectric materials. The HGI structure 30 in this example is made of alternating dielectric and conductive disk layers to form a HGI tube with a hollow center 40 for transporting the charged particles. This HGI structure is capable of withstanding high voltages generated by the Blumlein devices and, therefore, provides a suitable dielectric wall of the accelerator tube. The charged particle beam is introduced at one end of the accelerator tube for acceleration along the central axis of the HGI tube. FIGS. 2A-2C provide a time-series that is related to the state of the switch 12. As shown in FIGS. 2A-2C, a sleeve 28 fabricated from a dielectric material is molded or otherwise formed on the inner diameter of the single accelerator cell 10 to provide a dielectric wall. The cut up discs in FIGS. 2A to 2C are radial transmission lines. Each radial transmission line consists of a slow-medium disc and a fast-medium disc for propagation of signals, as will be described in detail below. In some systems, the DWA uses high gradient insulators (HGI), which is a layered insulator composed of alternating conductors and dielectrics. The HGI is capable of withstanding high voltages generated by the Blumlein or transmission line devices and, therefore, provides a suitable candidate for accelerator tube. A particle beam is introduced at one end of the dielectric wall 28 that accelerates along the central axis. The switch 12 is connected to allow the middle conductive plate 14 to be charged by a high voltage source. A laminated dielectric 20 with a relatively high dielectric constant separates the conductive plates 14 and 16. A laminated dielectric 22 with a relatively low dielectric constant separates the conductive plates 14 and 18. In the exemplary diagram of FIGS. 2A-2C, the middle conductive plate 14 is set closer to the bottom conductive plate 18 than to the top conductive plate 16, such that the combination of the different spacing and the different dielectric constants results in the same characteristic impedance on both sides of the middle conductive plate 14. Although the characteristic impedance may be the same on both halves, the propagation velocity of signals through each half is not the same. The higher dielectric constant half with laminated dielectric 20 is much slower. This difference in relative propagation velocities is represented by a short fat arrow 24 and a long thin arrow 25 in FIG. 2B, and by a long fat arrow 26 and a reflected short thin arrow 27 in FIG. 2C.

In a first position of the switch 12, as shown in FIG. 2A, both halves are oppositely charged so that there is no net voltage along the inner length of the assembly. After the lines have been fully charged, the switch 12 closes across the outside of both lines at the outer diameter of the single accelerator cell, as shown in FIG. 2B. This causes an inward propagation of the voltage waves 24 and 25 which carry opposite polarity to the original charge such that a zero net voltage will be left behind in the wake of each wave. When the fast wave 25 hits the inner diameter of its line, it reflects back from the open circuit it encounters. Such reflection doubles the voltage amplitude of the wave 25 and causes the polarity of the fast line to reverse. For only an instant moment more, the voltage on the slow line at the inner diameter will still be at the original charge level and polarity. As such, after the wave 25 arrives but before the wave 24 arrives at the inner diameter, the field voltages on the inner ends of both lines are oriented in the same direction and add to one another, as shown in FIG. 2B. Such adding of fields produces an impulse field that can be used to accelerate a beam. Such an impulse field is neutralized, however, when the slow wave 24 eventually arrives at the inner diameter, and is reflected. This reflection of the slow wave 24 reverses the polarity of the slow line, as is illustrated in FIG. 2C. The time that the impulse field exists can be extended by increasing the distance that the voltage waves 24 and 25 must traverse. One way is to simply increase the outside diameter of the single accelerator cell. Another, more compact way is to replace the solid discs of the conductive plates 14, 16 and 18 with one or more spiral conductors that are connected between conductor rings at the inner and/or outer diameters.

By arranging multiple DWA cells 10 over a continuous dielectric wall, the proton beam can be accelerated through the central axis of the multi-stage DWA by sequentially generating the appropriate voltage pulse for each section of the multi-stage DWA. As such, by timing the closing of the switches (as illustrated in FIGS. 2A to 2C), the generated electric field on the dielectric wall can be made to move at any desired speed. In particular, such a movement of the electric field can be made synchronous with the proton beam pulse that is input to the DWA, thereby accelerating the proton beam in a controlled fashion that resembles a "traveling wave" that is propagating down the DWA axis. It is advantageous to make the duration of these pulses as short as possible since the DWA can withstand larger fields for pulses with narrow durations.

The above DWA design in FIGS. 2A, 2B and 2C based on interleaved dielectric and conductor layers is only one exemplary DWA design. Various other DWA configurations can be used to produce the proper electric field for accelerating charged particles, including contiguous dielectric material shaped into tubular geometries.

Figures 3A, 3B:
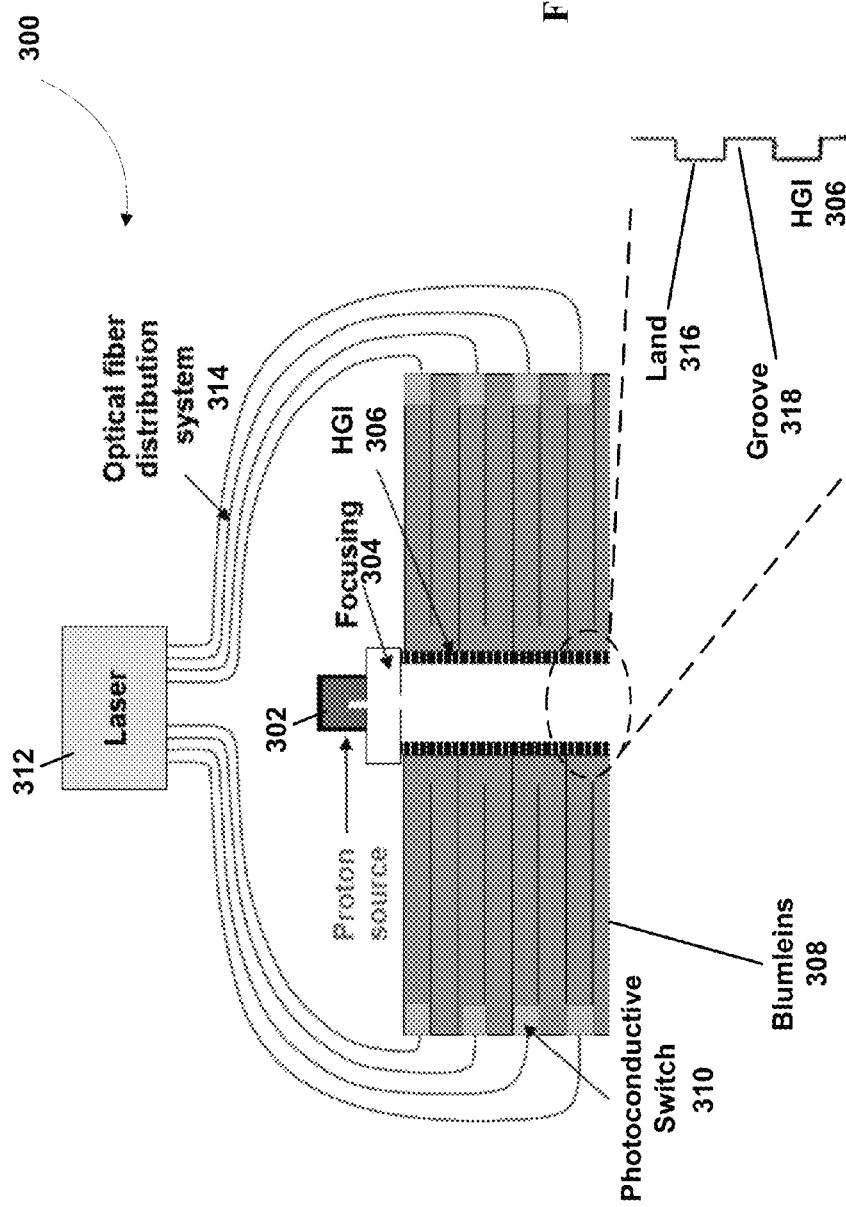
FIG. 3A illustrates an exemplary system that uses a grooved high gradient insulator (HGI) configuration.
FIG. 3B is an expanded view of the grooved HGI of FIG. 3A.

FIG. 3A illustrates another exemplary system 300 that uses an alternate HGI 306 configuration based a contiguous dielectric material tube. As illustrated in FIG. 3A, the proton beam from proton source 302 is coupled to the HGI 306 via focusing 304 elements. The stack of Blumleins 308 can be energized for each section of the HGI 306 through activation of photoconductive switches 310 that are connected to the laser 312 through a fiber optic system 314. A matching/transition rings, connecting the Blumleins 308 with the HGI 306, allow the voltage to be distributed azimuthally and uniformly distributed on the HGI. FIG. 3B illustrates an expanded view of a section of the HGI 306 to facilitate viewing of the grooves that are formed as part of the dielectric material. In contrast to the HGI in FIG. 2D that comprises a series of alternating dielectric and conductive layers 30 (the "multilayer HGI"), the HGI 306 of FIG. 3B uses contiguous dielectric material to form a cylinder with a hollow center in which the charged particles propagate and are accelerated. The sidewall of the HGI 306 includes alternating grooves 318 (i.e., depressions) and lands 316 (i.e., protrusions) that are formed as part of the dielectric material and in which the groove sidewalls are substantially parallel to the ends of the HGI 306 cylinder. Due to a difference between permittivities of the land and adjacent space within the grooves, the lands tend to deform the electrical field potential lines and produce an electric field that deflects the electrons away from the dielectric surface, thus improving the resistance of the dielectric material to vacuum flashover. The HGI 306 configuration that is depicted in FIGS. 3A and 3B (the "grooved HGI") and the multilayer HGI configuration that is depicted in FIG. 2D provide alternate HGI configurations that can be used in a charged particle accelerator. It should be noted that while FIG. 3B illustrates a land-to-groove periodicity of approximately 1-to-1 (i.e., the grooves and land have approximately the same widths), the grooved HGI can be fabricated with any land-to-groove periodicity as needed.

Figure 4A:
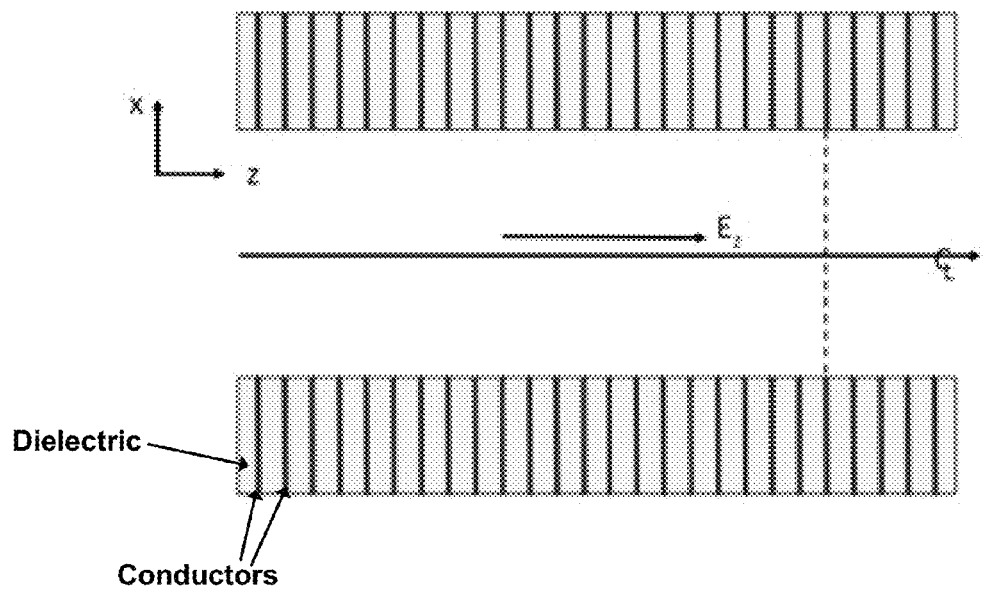
FIG. 4A illustrates a cross-sectional view of a normal multilayer HGI.
Figure 4B:
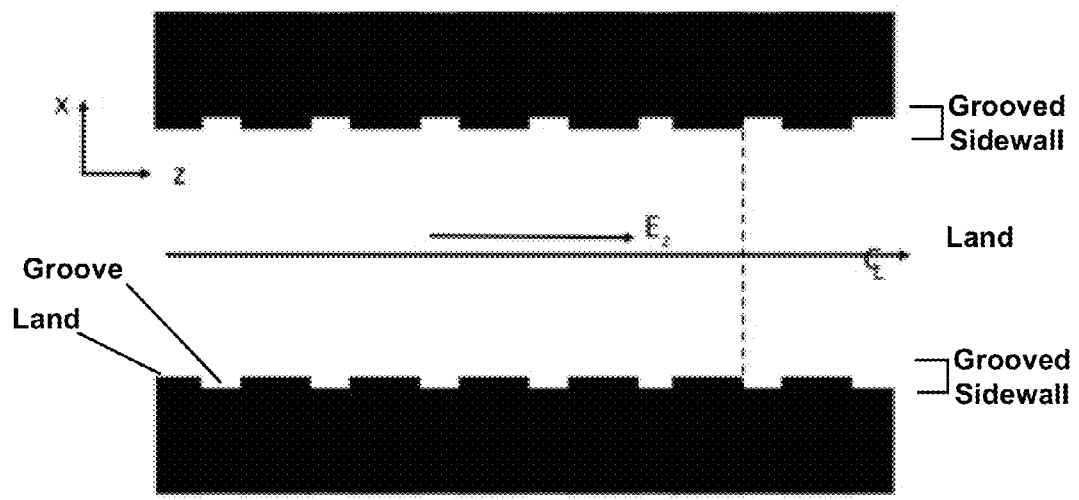
FIG. 4B illustrates a cross-sectional view of a normal grooved HGI.

FIG. 4A and FIG. 4B illustrate cross-sectional views of a multilayer HGI and a grooved HGI, respectively. FIGS. 4A and 4B illustrate the direction of an accelerating electric field, $E_z$, in the z-direction, along which a positively charged particle beam travels in the z-direction inside the hollow center of the DWA tube, along the longitudinal axis of the DWA tube. As illustrated in FIG. 4A, a normal HGI includes multilayer stacks of a dielectric material that are separated by thin conductors, or, as illustrated in FIG. 4B, includes grooved sidewalls, comprising alternating lands and grooves that are perpendicular to both the HGI surface and to its center axis. It should be noted that the stacked layers in FIG. 4A and the grooved sidewalls in FIG. 4B form continuous structures in the x-y plane, and the upper portion of these figures is part of the same continuous structure as the lower part in these figures.

Using the HGI configurations of FIGS. 4A and 4B (e.g., as part of the DWA 108 in FIG. 1), a positive charged particle beam enters the HGI from the left hand side, is accelerated in the z-direction as it travels through the center of HGI, and exits from the right side to ultimately reach the target area (e.g., a target tissue of a patient). As noted earlier, in order to scan a target area, such as a tumor, existing radiation therapy systems utilize a combination of large bending magnets, mechanical movement of certain large components of the radiation apparatus and movement of the patient's bed. These procedures are time consuming.

The disclosed embodiments provide HGI configurations that provide, in addition to the accelerating electric field along the longitudinal direction of the HGI tube, a transverse electric field that can be rapidly adjusted to deflect the charged particles in a direction perpendicular to the longitudinal direction (i.e. in a radial direction), thus allowing rapid beam scanning from shot-to-shot within one treatment session using components that are compact and lightweight. The transverse electric field for deflecting the charged particles can be generated by deforming the HGI in its geometry or position at one or more parts of the HGI. In some embodiments, scanning is carried out in response to a change in HGI's charging voltage, thereby enabling rapid changes in scan direction. Moreover, in accordance with the disclosed embodiments, a charged particle beam with any charge-to-mass ratio can be deflected based on the disclosed HGI configurations since, when the DWA operates in the "virtual traveling mode", a segment of the HGI would be turned on only when the charged particle beam arrives at that section of the DWA regardless of the charged particle's charge-to-mass ratio and regardless of whether or not the HGI is deformed in geometry or position to produce the transverse electric in the DWA for deflecting or scanning the charged particles.

Figure 5A:
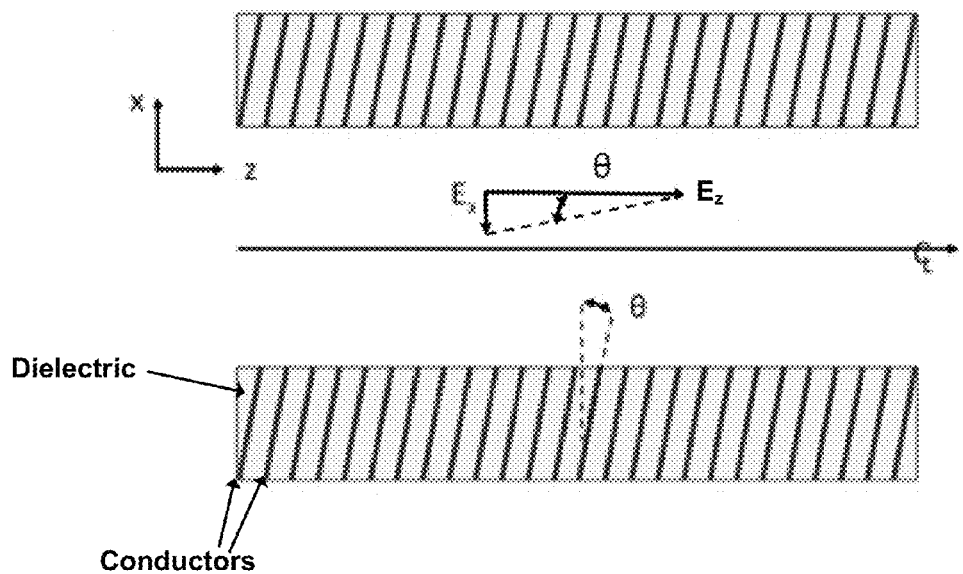
FIG. 5A illustrates a cross-sectional view of a deformed multilayer HGI in accordance with an exemplary embodiment.
Figure 5B:
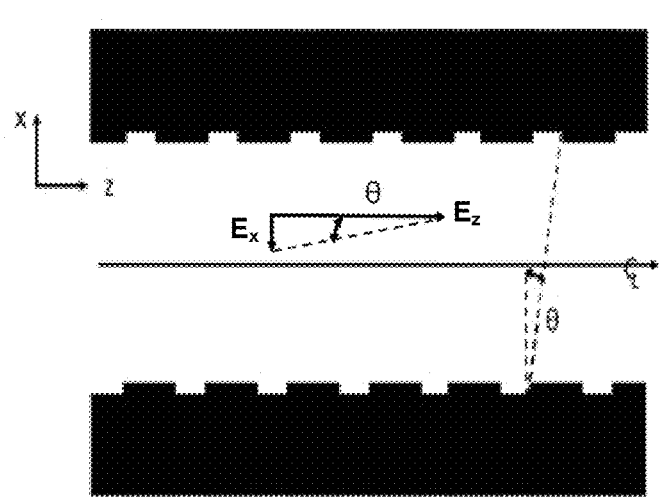
FIG. 5B illustrates a cross-sectional view of a deformed grooved HGI in accordance with an exemplary embodiment.
Figure 5C:
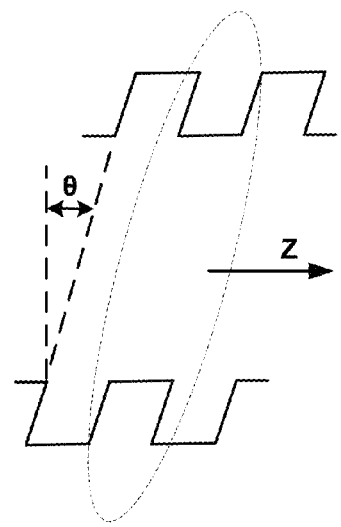
FIG. 5C illustrates an expanded view of the deformed grooved HGI of FIG. 5B in accordance with an exemplary embodiment.

FIGS. 5A and 5B illustrate an example of a deformed multilayer HGI and a deformed grooved HGI, respectively. The deformed multilayer HGI of FIG. 5A has conductors that are slightly slanted at an angle, θ, with respect to a radial axis normal to the longitudinal or z-axis. In the exemplary configurations of FIGS. 5A and 5B, the slant angle, θ, is illustrated with reference to x-axis. It is, however, understood that the deformed HGI of the disclosed embodiments can include a slant angle, θ, with respect to any radial axis, or combination of axis, in the x-y plane. Similarly, the deformed grooved HGI that is illustrated in FIG. 5B includes grooves that are slanted at an angle, θ, with respect to a radial axis normal to the longitudinal or z-axis. Unlike the grooved HGI of FIG. 4B, the land/grooves on opposite sides of FIG. 5B do not perfectly line up, but rather make an angle, θ, with respect to the equipotential dotted line that is drawn the edge of one land to the edge of the land on the opposite side. FIG. 5C is an expanded view of the grooves and lands of the deformed grooved HGI of FIG. 5B that provides a more detailed view of the slant angle, θ. Applying an electric voltage across the deformed HGIs of FIGS. 5A and 5B yields to an accelerating electric field, $E_z$, along the center axis and a small dipole field, $E_x$, perpendicular to the z-axis. Since the slant angle is small, $E_x \sim \theta E_z$, where θ is in radians. In some embodiments, the deformed HGIs of FIGS. 5A and 5B can be used to simultaneously accelerate (due to $E_z$) and deflect (due to $E_x$) a charged particle beam that travels through the center of the corresponding HGI. An HGI and/or DWA configuration that both accelerates and deflects a charged particle beam is referred to as an accelerating DWA dipole. Similar to the discussion in connection with FIGS. 4A and 4B, the stacked slanted layers in FIG. 4B and the slanted grooved sidewalls in FIGS. 5B and 5C form continuous structures in the x-y plane, and the upper portion of these figures is part of the same continuous structure as the lower part in these figures. For example, with reference to FIG. 5C, the grooves that are within the dashed circle form a single ring-shaped protrusion around the inside wall of the cylindrical-shaped DWA.

Figure 5D:
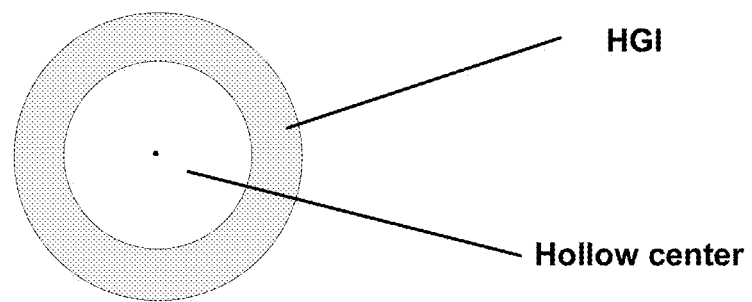
FIG. 5D illustrates a rotatable deformed HGI in accordance with an exemplary embodiment.
Figure 5D:
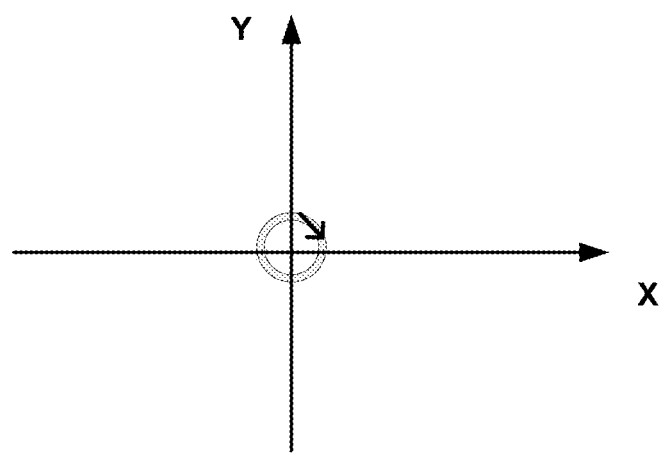

FIG. 5D is a cross-sectional view of a rotatable HGI in accordance with an exemplary embodiment. In FIG. 5D, the z-axis is pointing out of the page. The HGI in FIG. 5D can be a deformed HGI, such as the HGIs shown in FIG. 5A or FIG. 5B, or a deformable HGI, such as the HGI shown in FIG. 9. The HGI in FIG. 5D can be rotated around the z-axis as shown by the circular arrow. The direction of rotation can be clockwise and/or counter clockwise and the amount of rotation can be any amount that is desired. Rotating a deformed HGI (e.g., the deformed HGIs in FIGS. 5A and 5B) about the z-axis allows scanning of the charged particle in the x-y plane.

Figure 6:
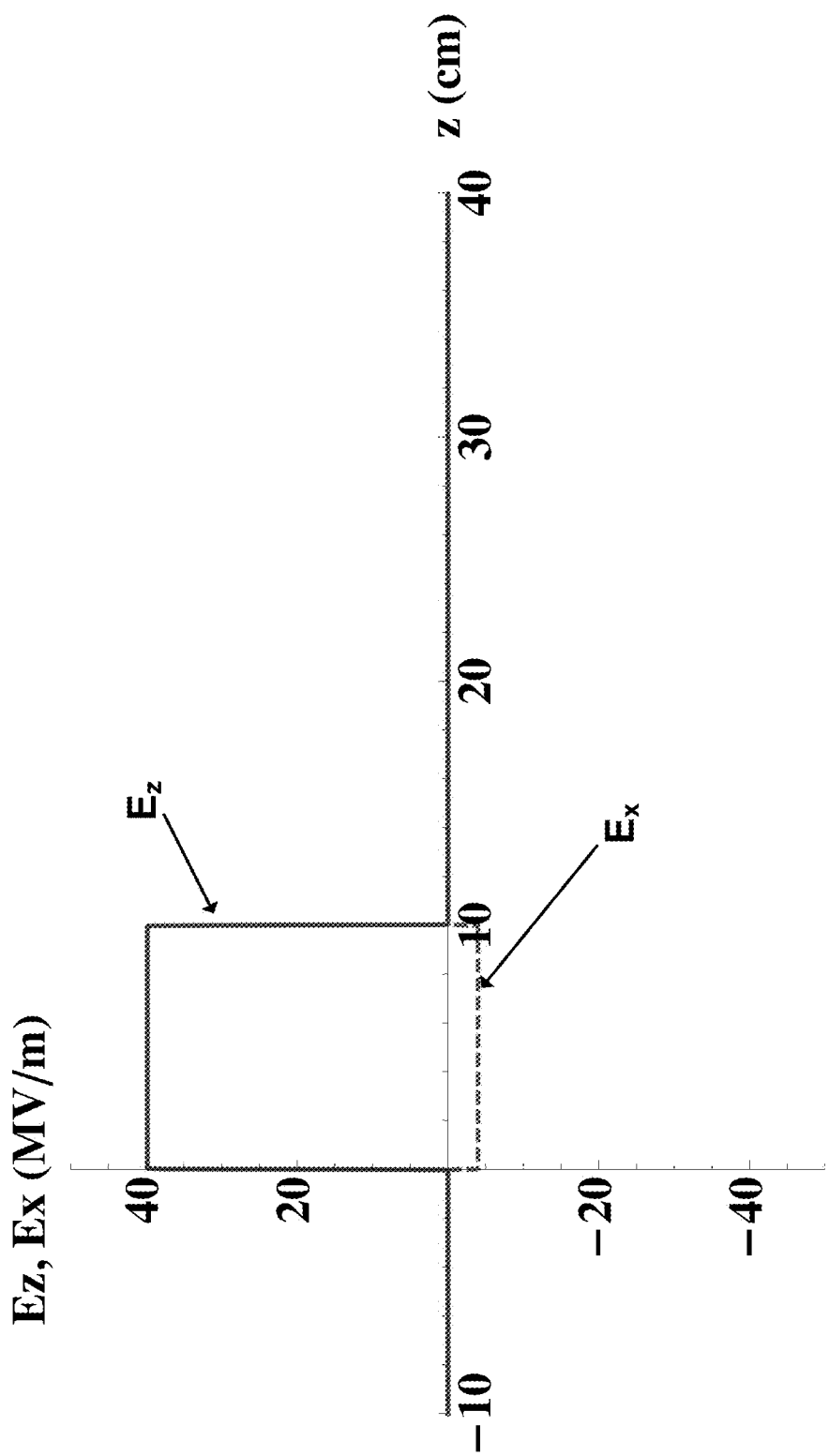
FIG. 6 illustrates accelerating and dipole fields of an "accelerating" DWA dipole in accordance with an exemplary embodiment.

FIG. 6 illustrates accelerating and dipole electric fields of an "accelerating" DWA dipole in accordance with an exemplary embodiment. The electric fields that are shown in FIG. 6 can be produced by, for example, the each of the deformed HGIs in FIGS. 5A and 5B. The solid line in FIG. 6 corresponds to the accelerating field gradient, $E_z$, that is 40 MV/m, for a 10-cm long deformed HGI configuration. The dashed line in FIG. 6 corresponds to the dipole field, $E_x$, that is 4 MV/m, for a small 0.1-radian slant angle, θ, with respect to the x-axis. It should be noted that the slant angle of 0.1 radians is only used to provide an example of the disclosed embodiments. However, other slant angles (e.g., 0.2 radians, etc.) may be used to produce dipole fields of varying strengths. The slant angle can be set at values below a threshold value where the dielectric material may breakdown due to presence of the transverse electric field. Nonetheless, if the slant angle is too large, the DWA dipole fails to successfully operate since the breakdown voltage of the HGI is reduced.

Figure 7A:
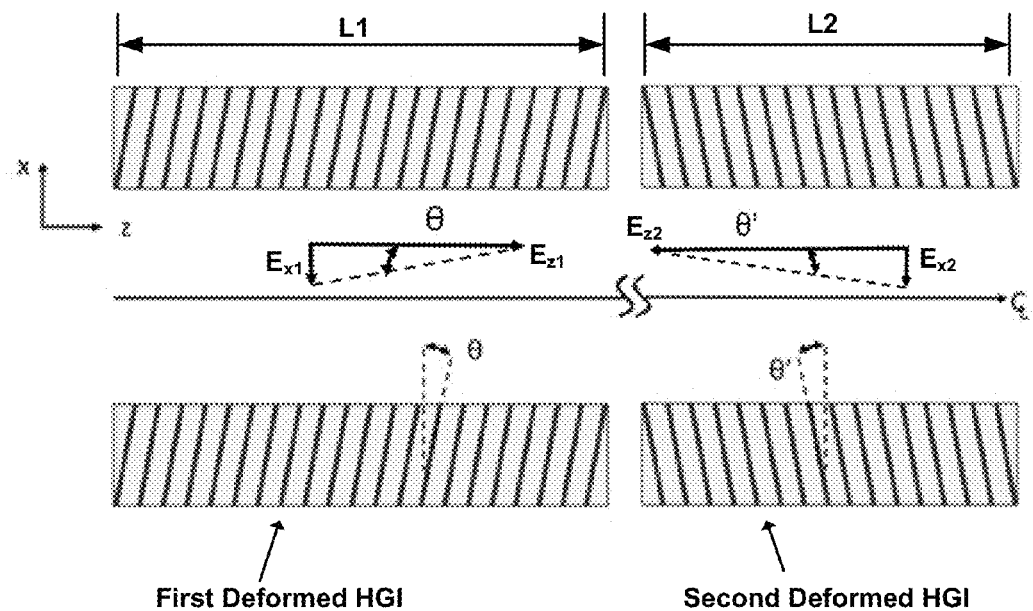
FIG. 7A illustrates a configuration with two deformed multilayer HGIs in accordance with an exemplary embodiment.

An accelerating DWA dipole can be used together with another DWA module with an opposite accelerating field. FIG. 7A shows a configuration with two deformed multilayer HGIs in accordance with an exemplary embodiment. In the configuration of FIG. 7A, the first deformed HGI and the second deformed HGI are both accelerating DWA dipoles and comprise conductors that are slanted at different slant angles and in opposite directions. The first and the second deformed HGIs in FIG. 7A produce dipole fields, $E_{x1}$ and $E_{x2}$, in the same direction to deflect the charged particle beam. The accelerating field, $E_{z1}$, produced by the first HGI FIG. 7A is in opposite direction of the accelerating field, $E_{z2}$, produced by the second HGI. The direction of the accelerating/decelerating electric fields is determined by the polarity of the voltage that is applied across the HGI, while the magnitude of the accelerating/decelerating electric fields is determined, at least in-part, by the amplitude of the applied voltage. It should be noted that FIG. 7A does not necessarily depict the correct scale for the first and the second deformed HGIs. In particular, in order to produce no net acceleration, the voltage or the axial field-length product of the first deformed HGI must be equal and opposite to that of the second deformed HGI, that is: $E_{z1} \times L1 = -(E_{z2} \times L2)$. Further, while the exemplary configuration of FIG. 7A depicts two deformed multilayer HGIs, it is understood that one or both of the first and second HGIs can be a deformed grooved HGI.

Figure 7B:
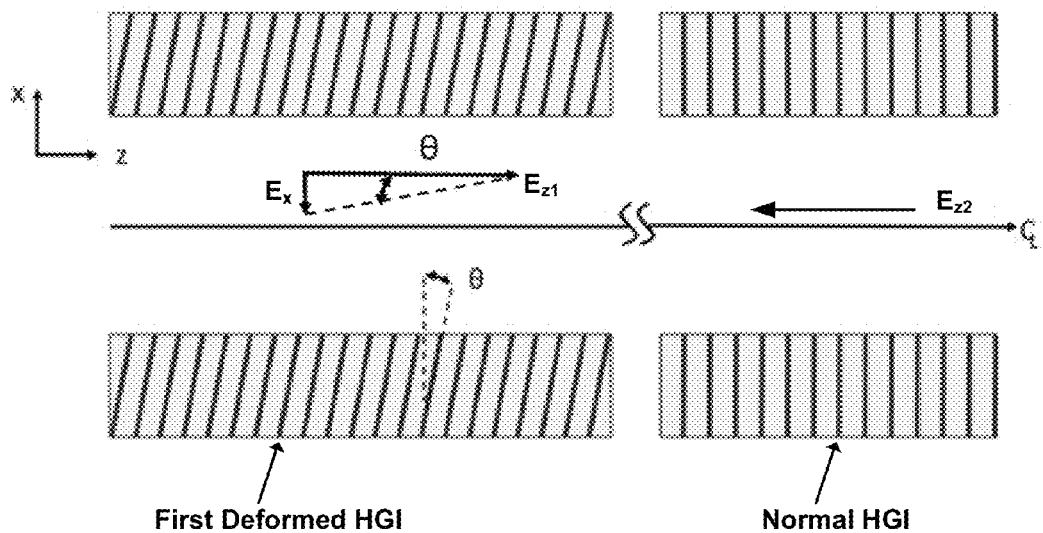
FIG. 7B illustrates a configuration with one deformed multilayer HGI and one normal multilayer HGI in accordance with an exemplary embodiment.

FIG. 7B shows a configuration with one deformed multilayer HGI on the left hand side and one "normal" multilayer HGI on the right hand side in accordance with an exemplary embodiment. The term "normal" in this context is used to designate an HGI with conductors/grooves that are substantially perpendicular to the z-axis. In the configuration of FIG. 7B, the first deformed HGI is an accelerating DWA dipole that comprises conductors that are slanted at an angle θ. The second HGI is a normal HGI that provides acceleration equal and opposite in direction to the acceleration provided by the first deformed HGI by, for example, applying voltages of equal amplitude and opposite polarity to the two deformed HGIs. The acceleration provided by each HGI can be obtained by multiplying $E_z$ by the length of the corresponding HGI.

Exemplary configurations in FIGS. 7A and 7B provide examples of a "pure" DWA dipole configuration that provides substantially no net acceleration for the charged particle beam traveling through the interior of the DWA. Such pure DWA dipole configurations can include normal, deformed, multilayer and/or grooved HGIs that are positioned in cascade. In some embodiments, by controlling the length and/or $E_z$, however, the DWAs can be configured to operate as an accelerating or decelerating dipole. Such accelerating DWA dipole configurations can include one or more normal, deformed, multilayer and/or grooved HGIs.

Figure 8:
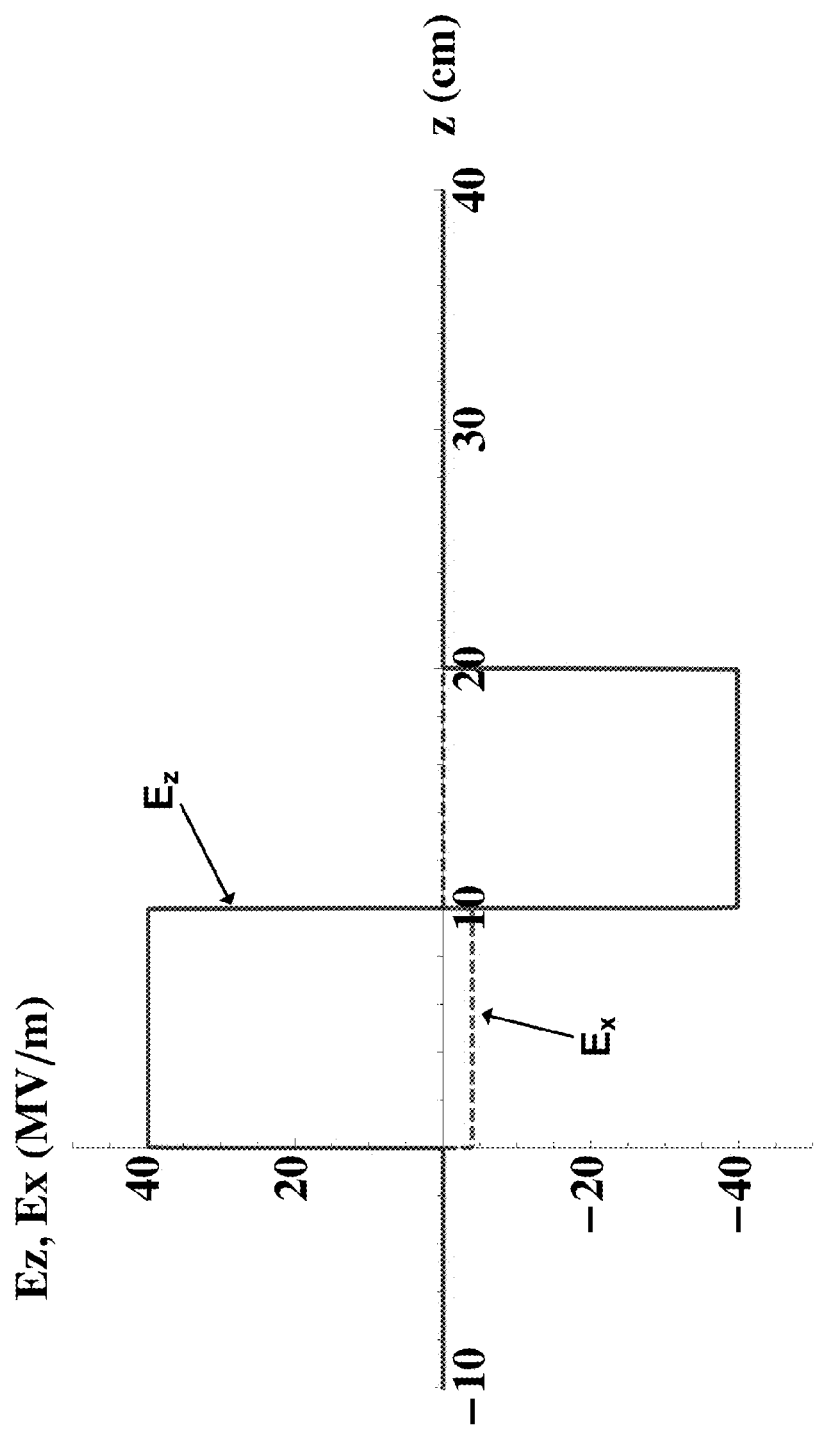
FIG. 8 illustrates accelerating and dipole fields of a "pure" DWA dipole in accordance with an exemplary embodiment.

FIG. 8 illustrates accelerating and dipole fields of a pure DWA dipole in accordance with an exemplary embodiment. The fields that are plotted in FIG. 8 can correspond to the configuration that is depicted in FIG. 7B. The solid line in FIG. 8 corresponds to the accelerating field gradient, $E_z$, that is 40 MV/m for a first 10-cm long deformed HGI and -40 MV/m for a 10-cm long normal HGI that is positioned in cascade next to the first deformed HGI with no drift space in between. The dashed line in FIG. 8 corresponds to the dipole field, $E_x$, that is 4 MV/m for the first deformed HGI with a small 0.1-radian slant angle, θ. Integrating the area under the $E_z$ field curve yields no net acceleration.

In some implementations, deflection of the charged particle beam can be adjusted by varying the voltage that is applied to the deformed HGI. Using such technique, the amount (i.e., degree) of beam deflection can be dynamically and rapidly adjusted.

Figure 9:
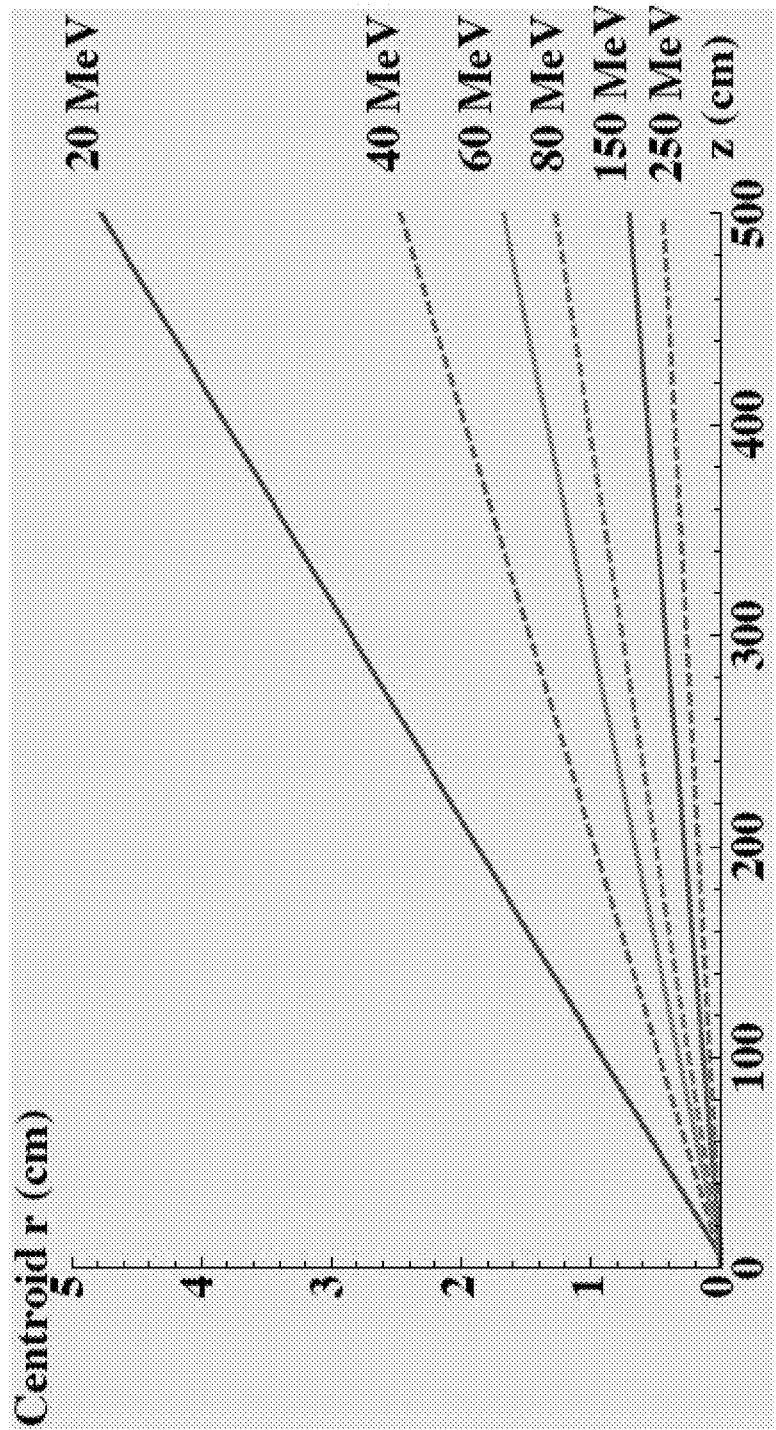
FIG. 9 illustrates a charged particle beam's displacement that traverses through a pure DWA dipole in accordance with an exemplary embodiment.

FIG. 9 shows a charged particle beam's displacement that traverses through a pure DWA dipole in accordance with an exemplary embodiment. In producing the plots of FIG. 9, a 10-cm long deformed HGI with 0.1-radian slant angle, and a 10-cm long normal HGI were used (e.g., as illustrated in the configuration of FIG. 7B), with ±40 MV/m axial field gradients, $E_z$, as depicted in FIG. 8. The plots of FIG. 9 illustrate displacements of a charged particle beam centroid for different initial beam energies, ranging from 20 MeV to 250 MeV, as a function of distance traveled by the charged particle beam in z-direction. Examination of FIG. 9 reveals that beams with lower energies can be deflected more easily compared to beams with higher energies. As such, in implementing a deformed HGI within a DWA of a hadron therapy machine (i.e., an intra-DWA beam deflector), it may be advantageous to position the deformed HGI close to the beginning of the DWA where the energies of the charged particles are relatively low to achieve the maximum beam scanning range. In some embodiments, however, the deformed HGI may be positioned at other locations within the DWA if maximum scanning range is not needed. The centroid displacements illustrated in FIG. 9 further indicate that, using a moderately high gradient field (e.g., 40 MV/m) on the HGI, beam deflection and scanning can be implemented using the disclosed deformed intra-DWA beam deflectors that are only a small fraction of a meter long.

Since the high-gradient insulator is capable of holding very high electric field stress, the electric dipole field inside a deformed HGI with a small slant angle can be large, which is then strong enough to meet the beam scanning needs for hadron therapy. To scan the beam from a displacement of $\Delta x$ to a displacement of $-\Delta x$, the polarity of the charging voltage(s) on the DWA dipole(s) can be changed. Scanning range can also be increased by placing additional deformed HGI in cascade with one or more existing deformed HGIs. For example, the scanning range of the configuration in FIG. 7A is twice that of the configuration in FIG. 7B. Both the accelerating and pure DWA dipoles can be placed either upstream, inside or downstream of an accelerator to effectuate beam deflection, depending on the requirements for the performance of beam scanning and transport. As demonstrated by FIG. 9, placing a pure DWA dipole with the field profile shown in FIG. 6 at the location that proton energy is 40 MeV can deflect the beam by ~2.5 cm. The amount of beam deflection is approximately linearly proportional to the slant angle and length of the deformed HGI, and inversely proportional to the beam energy. Therefore, doubling the slant angle or the length of the DWA dipole can double the centroid displacement.

The energy of a charged particle beam that propagates through a pure DWA dipole is not changed and thus the remaining sections of a beam transport system need not be modified. As such, the use of a pure DWA dipole enables decoupling of beam scanning from changing the beam energy and spot size on the patient. In implementations that utilize an accelerating DWA dipole, the charged particle beam is both deflected and accelerated as it travels through the DWA. Therefore, beam scanning from shot to shot by varying the charging voltage on the HGI can also affect the beam energy as it exits the accelerating DWA dipole, thereby affecting beam transport through the remaining sections of the accelerator system that is tuned for a specific energy. In such a scenario, other sections of the DWA may be modified to offset, or account for, beam energy variations. For example, an additional HGI section can be added to the end of DWA accelerator to reduce or increase the beam energy as it exits the accelerator.

In some embodiments that utilize a deformable multilayer HGI, in addition to, or instead of, varying the voltage that is applied to the deformed multilayer HGI, the slant direction and/or orientation of the multilayers can be changed to vary the transverse and axial fields.

Figure 10:
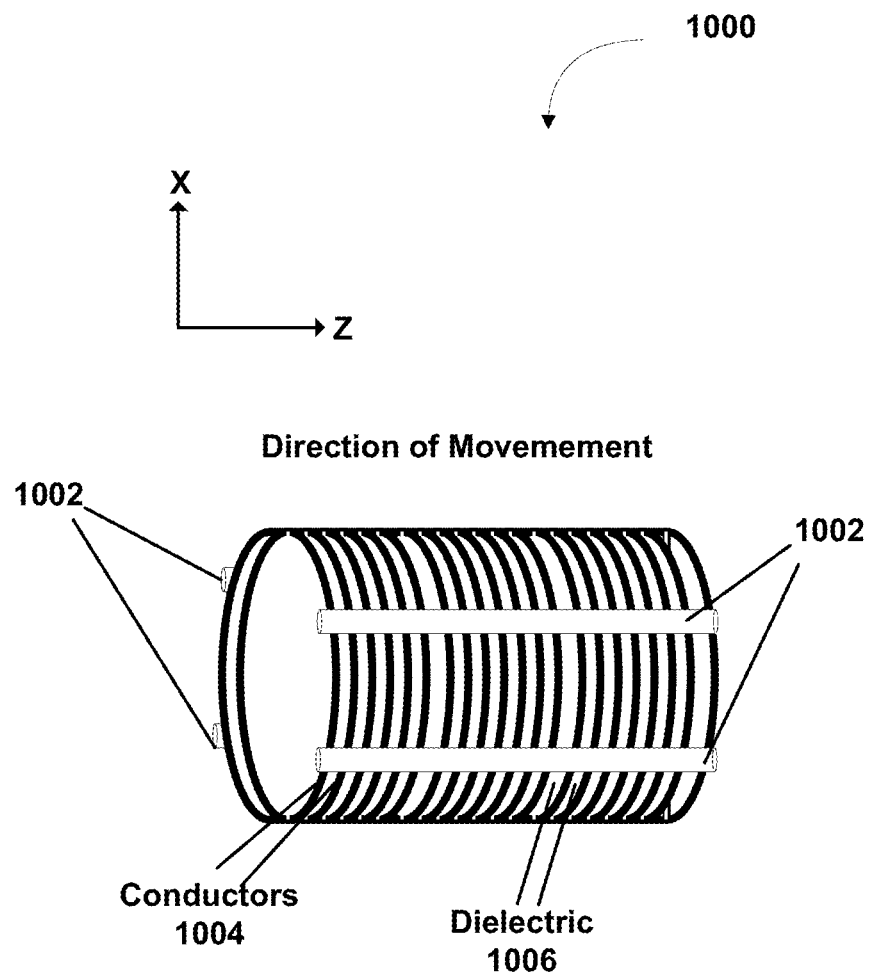
FIG. 10 illustrates a multilayer deformable HGI with moveable alternating conductors and dielectric sections.

FIG. 10 illustrates a multilayer deformable HGI 1000 that comprises alternating conductors 1004 and dielectric 1006 sections. One or more rods 1002 (or other control mechanisms) are attached to the multilayer stacks that allow at least the slant angle of the multilayer stack to be changed. The rods 1002 can, for example, be coupled to a stepper motor (or other electro-mechanical component) that operates to move the rods in a desired direction. In some embodiments, the deformable HGI includes "wavy" or "rippled" ring-shaped conductors for creating desired transverse focusing or defocusing electric fields for beam transport. The "wavy" or "rippled" ring-shaped conductors are made of suitable material that can be contorted or deformed in any particular orientation. In such embodiments, through a movement of one or more rods 1002, a deformed HGI with different cross-sectional forms and with any slant angle within any cross-section plane can be obtained. Therefore, in embodiments that utilize a deformable multilayer HGI 1000, beam scanning can be carried out by changing the applied voltage to the deformable HGI 1000 and/or changing the slant angle in any cross-sectional plane.

Figure 11A:
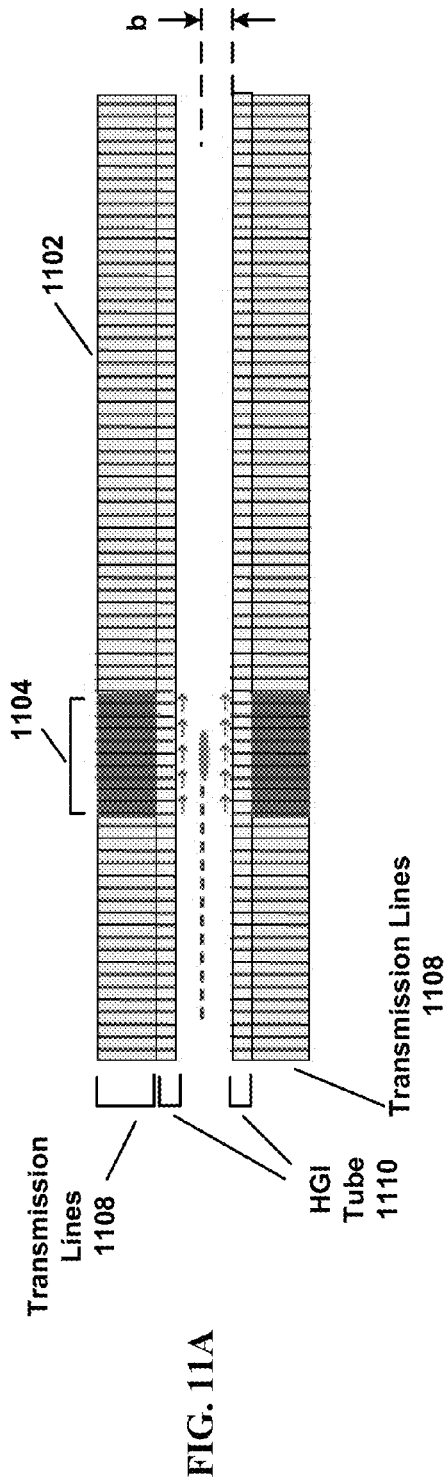
FIG. 11A illustrates a deformed HGI that forms a section of a larger DWA in accordance with an exemplary embodiment.
Figure 11B:
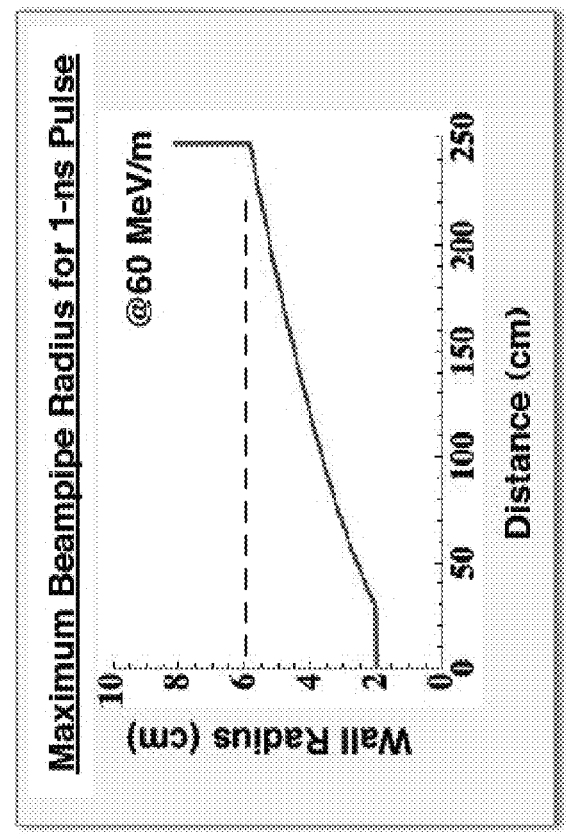
FIG. 11B is plot of DWA wall radius versus distance for a deflected charged particle beam corresponding to the DWA of FIG. 11A in accordance with an exemplary embodiment.

FIG. 11A illustrates a DWA 1102 with a corresponding section 1104 that comprises a deformed HGI in accordance with an exemplary embodiment. The inner cylinder is the HGI tube 1110 that is powered by transmission lines 1108. The deformed HGI section 1104 can comprise one or more deformed/deformable and normal HGIs that are used in a pure DWA dipole or accelerating/decelerating DWA dipole configurations. In the exemplary diagram of FIG. 11A, the deformed HGI section 1104 is located at approximately 30 cm from the entrance (i.e., left hand side) of the DWA 1102. The DWA 1102 wall radius, b, must be such that it accommodates the trajectory of the deflected particle beam as it travels through and exits the deformed HGI section 1104 and, further travels down the remaining sections of the DWA 1102. FIG. 11B illustrates the required wall radius of a DWA for a 1-ns voltage pulse and an axial field strength of 60 MV/m that accelerates and deflects a charged particle beam as it propagates through the DWA 1102. As a rule of thumb, the required wall radius to minimize the effects of fringe fields (which tend to reduce the on-axis acceleration field) is approximately three times the beam radius. In the exemplary configuration that is illustrated in FIG. 11B, a maximum wall radius of 6 cm is allowed at 250 cm from the entrance of DWA. To accommodate an increasing displacement of the deflected beam, a DWA with a larger (e.g., 6 cm) uniform radius may be used. Alternatively, a cone-shaped DWA with a progressively increasing wall radius (e.g., similar to the linear profile shown in FIG. 11B) can be implemented.

Figure 12:
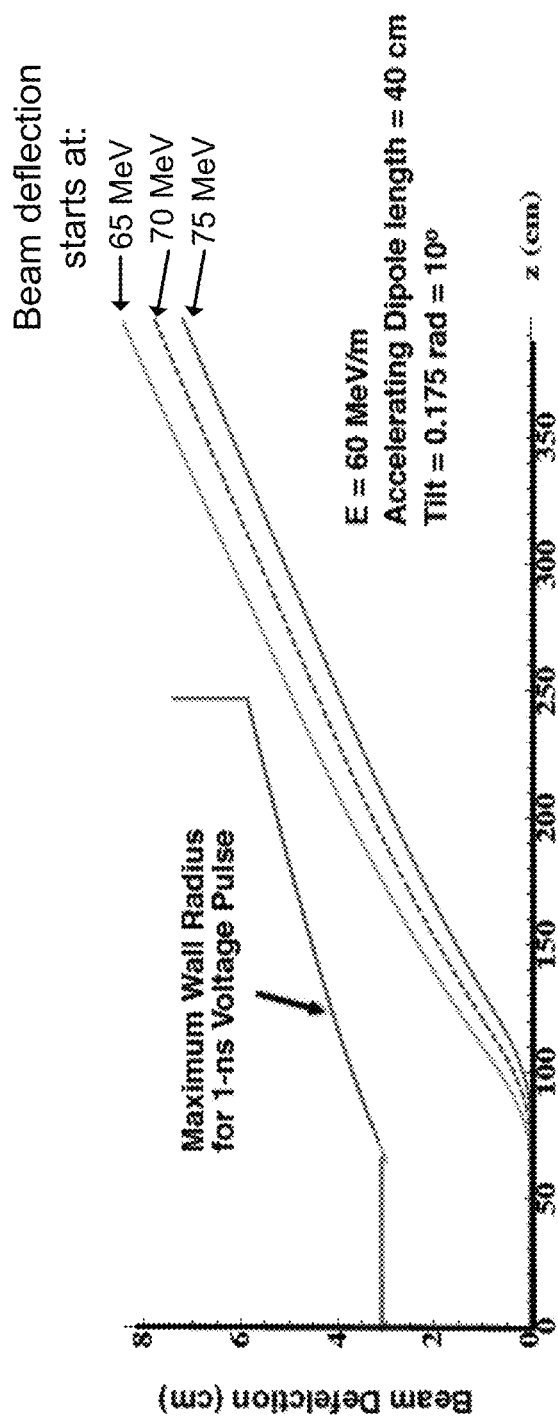
FIG. 12 illustrates a particle beam trajectory subsequent to deflection by a deformed HGI in accordance with an exemplary embodiment.

FIG. 12 illustrates a particle beam trajectory, superimposed on the DWA wall radius requirement, subsequent to particle beam's deflection by a deformed HGI in accordance with an exemplary embodiment. The maximum DWA wall radius resembles the plot illustrated in FIG. 11B. The plots of FIG. 12 correspond to scenarios in which deflection of the charged particle beam is carried out using an accelerating DWA dipole, with a length of 40 cm and a slant angle of approximately 0.175 radians. Examination of FIG. 12 confirms that beams with lower energies provide a larger scanning range (which also means deflecting a lower energy beam requires less dipole field).

Figure 13:
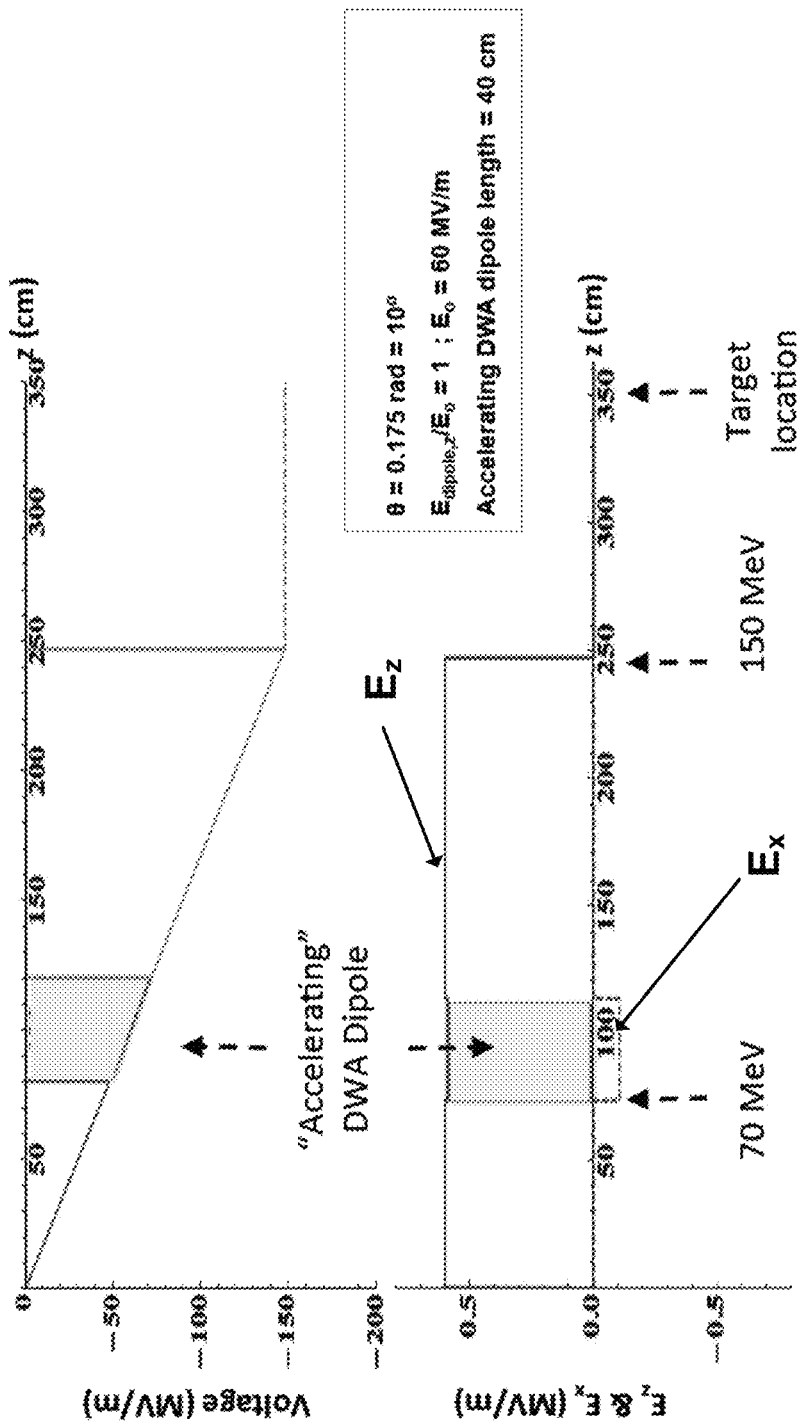
FIG. 13 illustrates voltage and electric fields as a function of axial distance in a DWA that utilizes an intra-DWA deflector in accordance with an exemplary embodiment.

FIG. 13 illustrates voltage and electric fields as a function of axial distance in a DWA that utilizes an intra-DWA deflector in accordance with an exemplary embodiment. The beam deflection is effected using an accelerating DWA dipole that is located in the middle of the DWA. The deformed HGI in the accelerating DWA dipole configuration of FIG. 13 is 40 cm long and has a slant angle of approximately 0.175 radians. The shaded section of FIG. 13 corresponds to the location of the accelerating DWA dipole. The top portion of FIG. 13 illustrates a linear voltage ramp across the DWA. The bottom section of FIG. 13 illustrates an approximately constant axial electric field, $E_z$ (solid line), across the DWA. The transverse electric field, $E_x$ (dashed line), is only present within the span of the accelerating DWA dipole section of the DWA.

Figure 14:
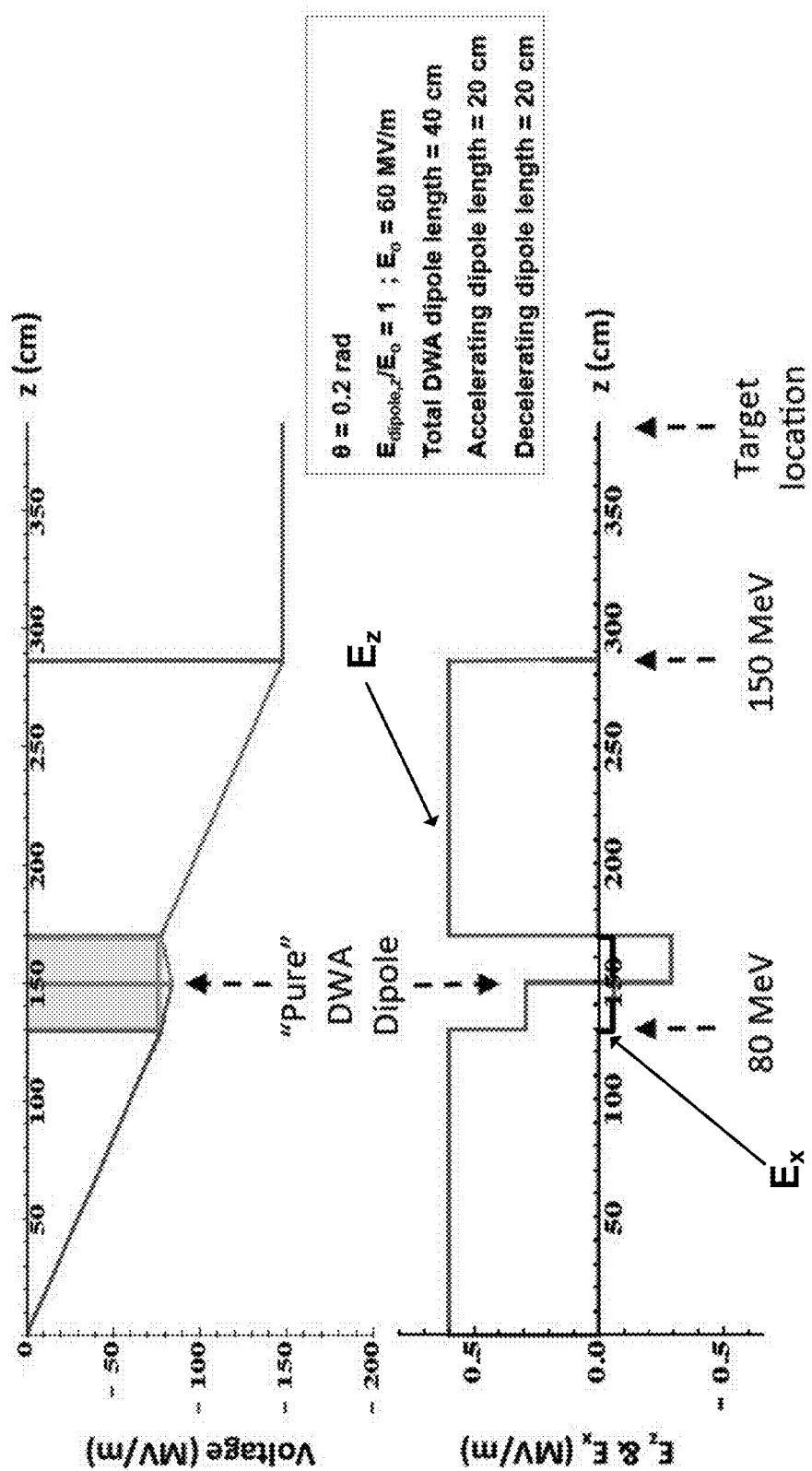
FIG. 14 illustrates voltage and electric fields as a function of axial distance in a DWA that utilizes an intra-DWA deflector in accordance with another exemplary embodiment.

FIG. 14 illustrates voltage and electric fields as a function of axial distance in a DWA that utilizes an intra-DWA deflector in accordance with another exemplary embodiment. The beam deflection is effected using a pure DWA dipole that is located in the middle of the DWA. The deformed HGI in the pure DWA dipole configuration of FIG. 14 is 40 cm long (a 20-cm accelerating dipole and a 20-cm decelerating dipole), with the accelerating dipole having a slant angle of approximately 0.2 radians. The shaded section of FIG. 14 corresponds to the location of the pure DWA dipole. The top portion of FIG. 14 illustrates the voltage characteristics across the DWA. The bottom section of FIG. 14 illustrates axial electric field, $E_z$ (solid line), across the DWA, as well as the transverse electric field, $E_x$ (dashed line), the latter only being present within the span of the pure DWA dipole section of the DWA.

Figure 15:
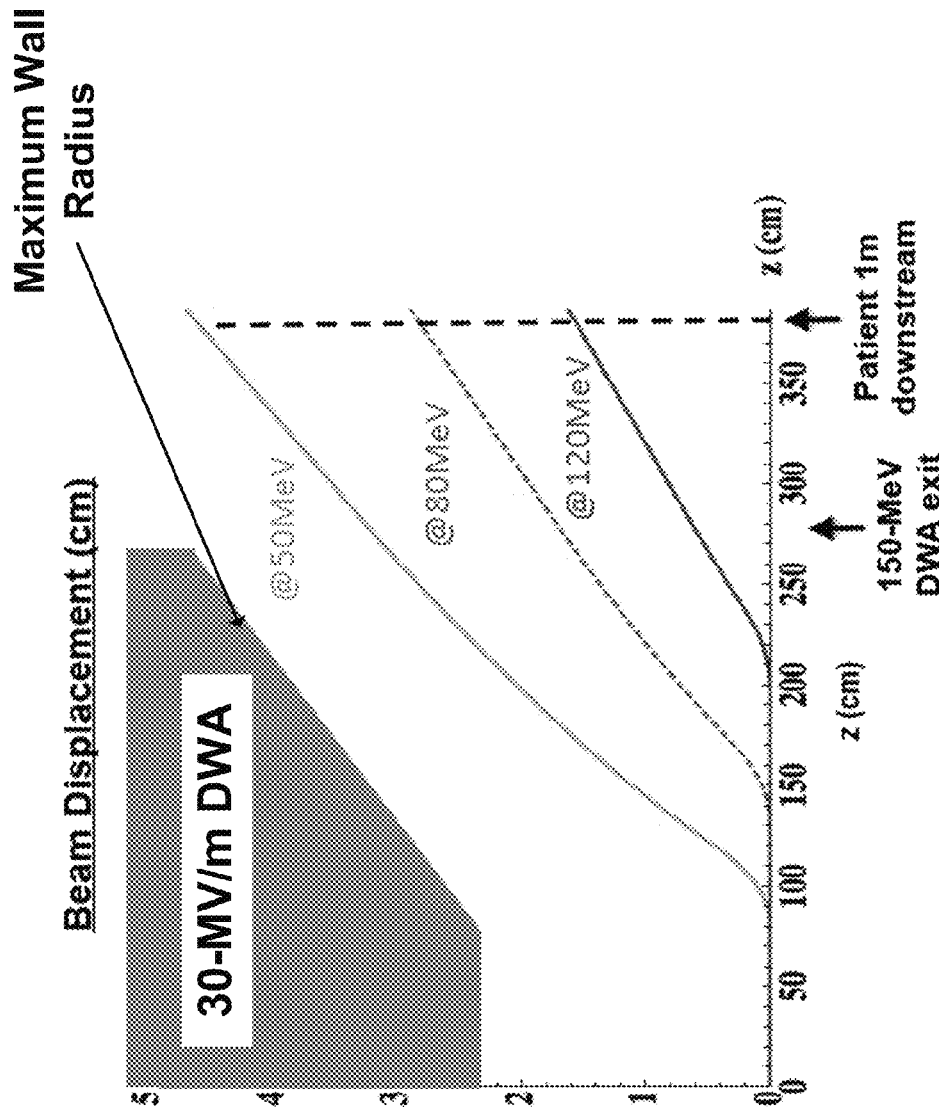
FIG. 15 illustrates a particle beam trajectory subsequent to particle beam's deflection by a deformed HGI in accordance with another exemplary embodiment.

FIG. 15 illustrates a particle beam trajectory, superimposed on the DWA wall radius requirement, subsequent to particle beam's deflection by a deformed HGI in accordance with another exemplary embodiment. The beam deflection is effected using a pure DWA dipole that is located in the middle of the DWA, with a slant angle of approximately 0.2 radians, and a 30 MV/m axial electric field. Examination of FIG. 15 reveals that, for a 50 MeV beam, approximately ±5 cm scanning range at the patient's location, assuming to be 1 meter from the 150-MeV DWA exit, can be achieved. Similar scanning range can be obtained if a pure DWA dipole with 0.1-radian tilt angle but 60 MV/m axial electric field is utilized. On the other hand, if a pure DWA dipole with 0.2-radian tilt angle and 60 MV/m axial electric field is utilized, ±8 cm scanning range at the patient's location can be achieved for a 60 MeV beam.

In addition to enabling scanning of a charged particle beam across a target of interest, the disclosed deformed HGIs can be used in applications that requires diversion and/or deflection of a charge particle beam, with or without changing the energy of the charged particles. For example, deformed HGIs that are described in the present application may be used to provide a switching mechanism for diverting a charged particle beam from one location to another location. In current radiation therapy systems, beam diversion is carried out by moving heavy-weight gantries. Using the disclosed deformed HGI configurations, charged particle beams may be diverted from one location to another location rapidly and accurately by simply changing the applied voltage values, rotating the deformed/deformable HGI, and/or moving the deformable multilayer HGI subsections.

Figure 16:
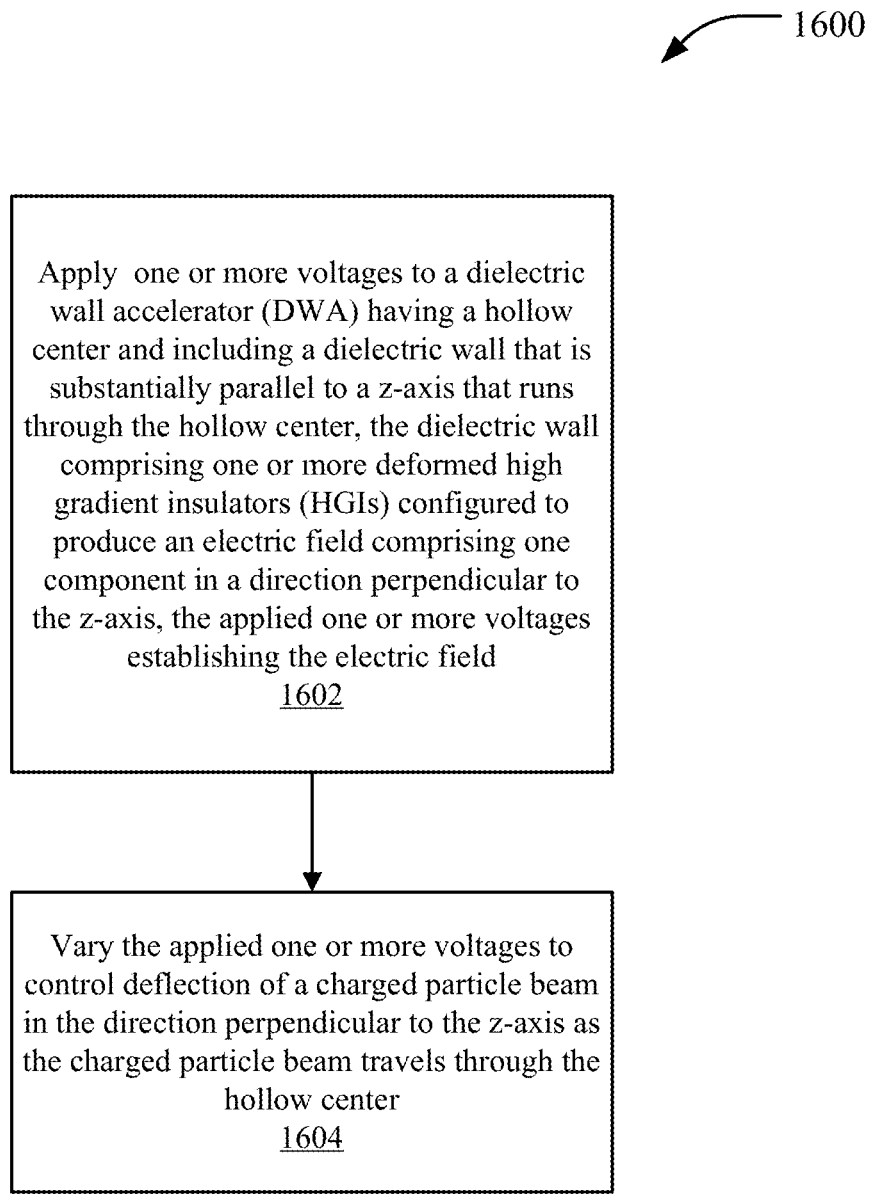
FIG. 16 illustrates a set of operations that can be carried out for scanning a charged particle beam in accordance with an exemplary embodiment.

FIG. 16 illustrates a set of operations 1600 that can be carried out for scanning a charged particle beam in accordance with an exemplary embodiment. At 1602, one or more voltages are applied to a dielectric wall accelerator (DWA) having a hollow center and including a dielectric wall that is substantially parallel to a z-axis that runs through the hollow center. The dielectric wall includes one or more deformed high gradient insulators (HGIs) that are configured to produce an electric field comprising one component in a direction perpendicular to the z-axis. The one or more voltages that are applied at 1602 establish the electric field including the component in the direction perpendicular to the z-axis. At 1604, the applied voltage(s) are varied to control deflection of a charged particle beam in the direction perpendicular to the z-axis as the charged particle beam travels through the hollow center. In some embodiments, additionally or alternatively, one or more HGIs can be rotated to control deflection of the charged particle beam in the direction perpendicular to the z-axis as the charged particle beam travels through the hollow center. In some embodiments, additionally or alternatively, one or more HGIs can be deformed to control deflection of the charged particle beam in a direction perpendicular to the z-axis as the charged particle beam travels through the hollow center.

It is understood that the various embodiments of the present disclosure may be implemented individually, or collectively, in devices comprised of various hardware and/or software modules, units and components. In describing the disclosed embodiments, sometimes separate components have been illustrated as being configured to carry out one or more operations. It is understood, however, that two or more of such components can be combined together and/or each component may comprise sub-components that are not depicted. Further, the operations that are described in the present application are presented in a particular sequential order in order to facilitate understanding of the underlying concepts. It is understood, however, that such operations may be conducted in a different sequential order, and further, additional or fewer steps may be used to carry out the various disclosed operations.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. For example, the exemplary embodiments have been described in the context of proton beams. It is, however, understood that the disclosed principals can be applied to other charged particle beams. Moreover, the generation of extremely short charged particle pulses that are carried out in accordance with certain embodiments may be used in a variety of applications that range from radiation for cancer treatment, probes for spherical nuclear material detection or plasma compression, or in acceleration experiments. The features of the embodiments described herein may be combined in all possible combinations of methods, apparatus, modules, systems, and computer program products.

What is claimed is:

1. A charged particle beam deflector, comprising:
a dielectric wall accelerator (DWA) having a hollow center and including a dielectric wall that is substantially parallel to a z-axis that runs through the hollow center, the dielectric wall comprising one or more deformed high gradient insulators (HGIs) configured to produce an electric field comprising a component in a direction perpendicular to the z-axis; and a control component configured to establish the component of the electric field in the direction perpendicular to the z-axis and to control deflection of a charged particle beam in the direction perpendicular to the z-axis as the charged particle beam travels through the hollow center; and an electro-mechanical component coupled to the one or more HGIs that comprises a deformable multilayer HGI comprising alternating dielectric and conductor materials that are arranged to form a changeable slant angle with respect to an axis normal to the z-axis, the electro-mechanical component operable to change the changeable slant angle of the deformable multilayer HGI to allow scanning of the charged particle beam at least in part based on the changeable scan angle when the slant angle is changed by the electro-mechanical component from one slant angle to another slant angle.

2. The charged particle beam deflector of claim 1, wherein the one or more HGIs comprise a deformed grooved HGI, the deformed grooved HGI comprising periodic grooves that are structured as part of a dielectric material and are arranged to form a slant angle, θ, with respect to an axis normal to the z-axis.

3. The charged particle beam deflector of claim 1, wherein the one or more HGIs comprise a deformed multilayer HGI comprising alternating dielectric and conductor materials that are arranged to form a slant angle, θ, with respect to an axis normal to the z-axis.

4. The charged particle beam deflector of claim 1, wherein:
the DWA comprises a first deformed HGI and a second HGI arranged in a cascade fashion; and
the control component is configured to establish:
at least a portion of the component of the electric field in the direction perpendicular to the z-axis across the first deformed HGI,
a first axial component of the electric field along the z-axis across the first deformed HGI, and
a second axial component of the electric field along the z-axis across the second HGI that is opposite in direction to the first axial component.

5. The charged particle beam deflector of claim 4, wherein the control component is configured to establish the first and the second axial components such that the charged particle beam experiences substantially zero net acceleration after traveling through the hollow center of both HGIs.

6. The charged particle beam deflector of claim 4, wherein the second HGI is one of a normal HGI, a deformable HGI or a deformed HGI.

7. The charged particle beam deflector of claim 1, wherein:
the DWA comprises a first deformed grooved HGI; and
the control component is configured to establish:
at least a portion of the component of the electric field in the direction perpendicular to the z-axis across the deformed grooved HGI, and
a first axial component of the electric field along the z-axis across the first deformed grooved HGI.

8. The charged particle beam deflector of claim 1, wherein the control component is configured to apply one or more voltages to the DWA for establishing the electric field.

9. The charged particle beam deflector of claim 8, wherein the control component is configured to vary the applied voltage(s) to modify the electric field strength.

10. The charged particle beam deflector of claim 1, wherein the electro-mechanical component is configured to rearrange physical characteristics of the deformable HGI, and to thereby change at least the slant angle of alternating dielectric and conductor materials of the deformable HGI with respect to the axis normal to the z-axis.

11. The charged particle beam deflector of claim 1, wherein at least one of the one or more deformed HGIs is configured to be rotated around the z-axis.

12. A radiation therapy system comprising the charged particle beam deflector of claim 1.

13. The radiation therapy system of claim 12, wherein the one or more deformed HGIs constitute a section of the DWA that includes additional sections comprising normal HGIs.

14. The radiation therapy system of claim 12, wherein the one or more deformed HGIs constitute a mechanism for diverting the charged particle beam from one therapy room to another therapy room and/or around a patient's location.

15. The radiation therapy system of claim 12, wherein the charged particle beam deflector is configured to allow scanning of the charged particle beam across a target area.

16. A method for scanning a charged particle beam, comprising:
applying one or more voltages to a dielectric wall accelerator (DWA) having a hollow center and including a dielectric wall that is substantially parallel to a z-axis that runs through the hollow center, the dielectric wall comprising one or more deformed high gradient insulators (HGIs) configured to produce an electric field comprising a component in a direction perpendicular to the z-axis, the applied one or more voltages establishing the electric field, the DWA comprising an electro-mechanical component coupled to the one or more HGIs that comprises a deformable multilayer HGI comprising alternating dielectric and conductor materials that are arranged to form a changeable slant angle with respect to an axis normal to the z-axis, the electro-mechanical component operable to change the changeable slant angle of the deformable multilayer HGI to allow scanning of the charged particle beam at least in part based on the changeable slant angle;
changing the changeable slant angle the electro-mechanical component from one slant angle to another slant angle to rearrange physical characteristics of the deformable HGI; and
varying the applied one or more voltages to control deflection of a charged particle beam in the direction perpendicular to the z-axis as the charged particle beam travels through the hollow center.

17. The method of claim 16, wherein:
the DWA comprises a deformed grooved HGI, the deformed grooved HGI comprising periodic grooves that are structured as part of a dielectric material and are arranged to form a slant angle, θ, with respect to an axis normal to the z-axis; and
varying the applied one or more voltages varies the strength of the electric field component in the direction perpendicular to the z-axis.

18. The method of claim 16, wherein:
the DWA comprises a deformed multilayer HGI comprising alternating dielectric and conductor materials that are arranged to form a slant angle, θ, with respect to an axis normal to the z-axis; and
varying the applied one or more voltages varies the strength of the electric field component in the direction perpendicular to the z-axis.

19. The method claim 16, wherein:
varying the applied one or more voltages varies the strength of the electric field component in the direction perpendicular to the z-axis.

20. The method claim 16, wherein:

the DWA comprises a first deformed HGI and a second HGI arranged in a cascade fashion; and applying the one or more voltages comprises:

applying a first voltage to establish at least a portion of the component of the electric field in the direction perpendicular to the z-axis across the first deformed HGI and a first axial component of the electric field along the z-axis across the first deformed HGI, and applying a second voltage to establish a second axial component of the electric field along the z-axis across the second HGI that is opposite in direction to the first axial component.

21. The method claim 20, wherein the first and the second voltage values are selected to establish the first and the second axial components such that the charged particle beam experiences substantially zero net acceleration after traveling through the hollow center of both HGIs.

22. The method of claim 16, wherein:

the DWA comprises a first deformed grooved HGI; and applying the one or more voltages comprises applying a first voltage to establish at least a portion of the component of the electric field in the direction perpendicular to the z-axis across the first deformed grooved HGI and a first axial component of the electric field along the z-axis across the first deformed grooved HGI.

23. The method of claim 16, wherein varying the one or more voltages comprises:

applying a first voltage to establish a first electric field component in the direction perpendicular to the z-axis and to thereby cause the charged particle beam to be deflected to a first position in an x-y plane that is perpendicular to the z-axis; and applying a second voltage to establish a second electric field component in the direction perpendicular to the z-axis and to thereby cause the charged particle beam to be deflected to a second position in the x-y plane.

24. The method of claim 16, wherein the changing the changeable slant angle comprises causing physical movement of alternating dielectric and conductor materials of the deformable HGI to change the changeable slant angle of the of alternating dielectric and conductor materials with respect to an axis normal to the z-axis, and to control the deflection of the charged particle beam.

25. The method of claim 16, further comprising rotating at least one of the one or more HGIs to cause the charged particle beam's deflection from a first location to a second location in an x-y plane that is perpendicular to the z-axis.

* * * * *